(12) United States Patent
Li et al.

(10) Patent No.: US 8,252,796 B2
(45) Date of Patent: Aug. 28, 2012

(54) 1-BUTYL-2-HYDROXYARALKYL PIPERAZINE DERIVATIVES AND THE USES AS ANTI-DEPRESSION MEDICINE THEREOF

(75) Inventors: Jianqi Li, Shanghai (CN); Na Lv, Shanghai (CN); Hua Jin, Shanghai (CN); Zhijie Weng, Shanghai (CN); Yongyong Zheng, Shanghai (CN)

(73) Assignees: CSPC Zhonggi Pharmaceutical Technology (Shijiazhuang) Co. Ltd. (CN); Shanghai Institute of Pharmaceutical Industry (CN)

( * ) Notice: Subject to any disclaimer, the term of this patent is extended or adjusted under 35 U.S.C. 154(b) by 0 days.

(21) Appl. No.: 13/122,691

(22) PCT Filed: Sep. 29, 2009

(86) PCT No.: PCT/CN2009/074314
§ 371 (c)(1),
(2), (4) Date: Apr. 5, 2011

(87) PCT Pub. No.: WO2010/040315
PCT Pub. Date: Apr. 15, 2010

(65) Prior Publication Data
US 2011/0183996 A1 Jul. 28, 2011

(30) Foreign Application Priority Data
Oct. 7, 2008 (CN) .......................... 2008 1 0043821

(51) Int. Cl.
*A61K 31/495* (2006.01)
*C07D 241/04* (2006.01)
(52) U.S. Cl. ............. 514/252.12; 514/255.03; 544/401; 544/394
(58) Field of Classification Search ............. 514/255.03, 514/252.12; 544/394, 401
See application file for complete search history.

(56) References Cited

U.S. PATENT DOCUMENTS

| 7,326,710 B2 | 2/2008 | Li et al. |
| 7,576,086 B2 | 8/2009 | Li et al. |
| 2005/0267121 A1 | 12/2005 | Li et al. |

FOREIGN PATENT DOCUMENTS

| CN | 1381448 A | 11/2002 |
| CN | 1384102 A | 12/2002 |
| CN | 1948297 A | 4/2007 |

OTHER PUBLICATIONS

"International Application Serial No. PCT/CN2009/074314, International Search Report mailed Jan. 7, 2010", (w/ English Translation), 8 pgs.
"European Application Serial No. EP09818779.2, Supplementary European Search Report mailed Mar. 6, 2012", 5 pgs.

*Primary Examiner* — Kristin Bianchi
(74) *Attorney, Agent, or Firm* — Schwegman, Lundberg & Woessner, P.A.

(57) ABSTRACT

The invention discloses 1-butyl-2-hydroxyl aralkyl piperazine derivatives and their use as antidepressants. The derivatives of the present invention have triple inhibition effect on the reuptake of 5-HT, NA and DA, and can be administrated to the patients in need thereof in form of composition by route of oral administration, injection and the like. Compared with clinically currently used dual targets antidepressants (such as venlafaxine), said derivatives may have stronger antidepression effect, broader indications, faster onset and lower neurotoxicity and side reaction; and said derivatives have stronger antidepression activity, lower toxicity, higher bioavailability, longer half life and better druggablity, compared with aryl alkanol piperazine derivatives and optical isomers thereof disclosed in prior art. The 1-butyl-2-hydroxyl aralkyl piperazine derivative is the free alkali or its salt of a compound of formula below:

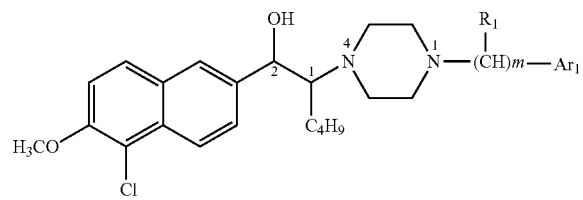

11 Claims, No Drawings

1-BUTYL-2-HYDROXYARALKYL PIPERAZINE DERIVATIVES AND THE USES AS ANTI-DEPRESSION MEDICINE THEREOF

RELATED APPLICATIONS

This application is a nationalization under 35 U.S.C. 371 of PCT/CN2009/074314, filed Sep. 29, 2009 and published as WO 2010/040315 A1 on Apr. 15, 2010, which claimed priority under 35 U.S.C. 119 to Chinese Patent Application No. 200810043821.8, filed Oct. 7, 2008; which applications and publication are incorporated herein by reference in their entirety.

FIELD OF INVENTION

The present invention relates to 1-butyl-2-hydroxyaralkyl piperazine derivatives and their use as broad-spectrum antidepressants.

BACKGROUND OF THE INVENTION

Depression is a syndrome characterized by significant and lasting low mood, which mainly manifests as affective disorder. The symptoms include low mood, less speech, slow mentality and motion, and even suicide attempt. Depression, as a chronic mental disease, has become a fiendish problem which bothers the medical health service in China, due to long treatment course, slow effect onset and higher rate of relapse, disability and suicide. According to "World Health Reports" announced by World Health Organization (WHO), depression has become the fourth largest disease in the world, and depression might become the second largest illness after heart disease in 2020, and thus become a serious problem to human health.

So far, the action mechanism of antidepressant has not been clearly demonstrated. Drugs having definite effect substantially act on synapses of the nerve ending, and exert their curative effects by adjusting the level of neurotransmitters in synaptic cleft. The biochemistry study on etiology indicated that depression relates mainly to five types of neurotransmitters, i.e., central 5-hydroxytryptamine (5-HT), noradrenaline (NA), dopamine (DA), acetylcholine (Ach), and γ-aminobutyric acid (GABA).

Antidepressant can be divided into two categories: early non-selective antidepressants and novel selective reuptake inhibitors. Non-selective antidepressants mainly include monoamine oxidase inhibitors (MAOIs) and tricyclic antidepressants (TCAs); selective reuptake inhibitors mainly comprise selective 5-hydroxytryptamine (5-HT) reuptake inhibitors (SSRIs), noradrenaline (NA) reuptake inhibitors (NRIs), noradrenergic and specific 5-HT reuptake inhibitors (NDRIs), 5-HT and NA dual reuptake inhibitors (SNRIs), 5-HT re-absorption enhancers, and the like.

Early monoamine oxidase inhibitors and tricyclic antidepressants have serious adverse reactions; as for the subsequent selective NA reuptake inhibitors and selective 5-HT reuptake inhibitors, although they have less adverse reactions, disadvantages such as slow onset, indefinite efficacy and the like, still exist. Therefore, the effects of all kinds of drugs above in treating depression are not satisfactory. So far, the existing antidepressants still can not meet the demand of clinical treatment.

Venlafaxine, the first 5-HT and NA dual reuptake inhibitor marketed in American in 1997, and dutoxetine marketed in 2004 have advantages of rapid onset of action, compared with selective 5-hydroxytryptamine reuptake inhibitors such as fluoxetine, and noradrenaline reuptake inhibitors such as reboxetine, and have significant effects on both serious depression and refractory depression. From venlafaxine on, development on the novel antidepressants that have 5-HT and NA dual action routes, faster onset, fewer side effects and stronger effect, becomes the research emphasis and an important development direction.

At present, many studies indicate that the addition of DA reuptake inhibitors in dual reuptake inhibitors can obtain better antidepression effect. 5-HT, NA and DA triple selective reuptake inhibitors (also known as "broad-spectrum" antidepressants), developed based on dual reuptake inhibitors, are now still in clinical research phase. For example, triple selective reuptake inhibitor DOV-216303 developed by DOV Pharmaceutical Inc. is in phase III clinical trial; NS-2359 developed jointly by GlaxoSmithKline and NeuroSearch Inc. is now in phase II clinical trial of antidepressant. These monoamine transmitter triple selective reuptake inhibitors possess advantages of high effectiveness and fast onset and are becoming hot points in the antidepressants development.

The applicant has disclosed aryl alkanol piperazine derivatives and their use in preparation of antidepressants in Chinese patent ZL02111934.1. A preferred compound therein, $N^1$-benzyl-$N^4$-[1-methyl-2-(5'-chloro-6'-methoxyl-2'-naphthyl) hydroxyethyl]piperazine (IV-19, SIPIyy24, see formula A below), has a dual inhibition effect on the reuptake of 5-HT and NA, and has a strong antidepression biologic activity on animals. But a further research finds that the antidepression effect thereof is still not so satisfactory and adverse reaction thereof is obvious.

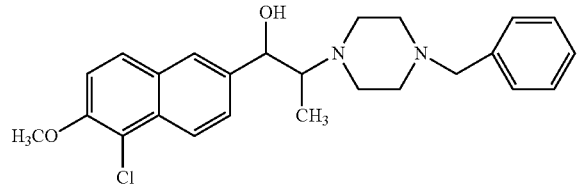

Formula A

Subsequently, the applicant disclosed the optical isomers of compound SIPIyy24 and the use thereof in Chinese patent ZL 200510030354.1. Study shows that the (1S,2R) optical isomer of SIPIyy24 (code SIPI5286) has an inhibition effect on the reuptake of the three kinds of monamine transmitters, i.e. 5-HT, NA and DA. It is a novel triple reuptake inhibitor, and has better antidepression activity and safety than that of the racemate, and is worthy of being a novel antidepressant. However, it is found through further studies that, the half life of SIPI5286 is too short, and thus not suitable to be formulated into a medicament.

DESCRIPTION OF THE INVENTION

One of the technical problems to be resolved in the present invention is to disclose a 1-butyl-2-hydroxyl aralkyl piperazine derivative to overcome the defects in the prior art, i.e., low efficacy, prominent side effects and slow onset, and thus resolve the clinical problem and meet the requirements of clinical application.

Another technical problem to be resolved in the present invention is to disclose the use of above mentioned derivative in the preparation of antidepressants.

The 1-butyl-2-hydroxyl aralkyl piperazine derivative mentioned in the present invention is the free alkali or its salt of compound of formula (1), or the free alkali or its salt of the optical isomers of compound of formula (1):

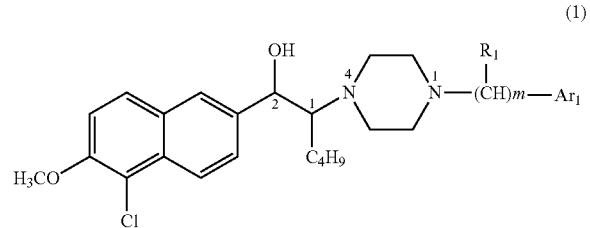

wherein:

Ar₁ represents benzene; substituted phenyl; a 5-member or 6-member aromatic heterocycle containing N, O or S, or cinnamenyl, wherein the substituted phenyl is a phenyl containing one to four (1, 2, 3 or 4) substituents on the benzene ring, wherein the substituents are halogen, hydroxyl, alkyl, nitro, alkoxy or amino;

m is an integer of 0~5, preferably 0 or 1;

$R_1$ represents hydrogen, $C_1$-$C_5$ alkyl (preferably $C_1$-$C_3$ alkyl and more preferably methyl), $C_5$ or $C_6$ alicyclic ring, benzene, substituted phenyl, hydroxyl, amino, substituted amino, $C_1$-$C_4$ alkoxy, $C_1$-$C_4$ acyl, halogen, carboxylic acid or carboxylic ester, wherein, the substituted amino is an amino substituted by $C_1$-$C_4$ alkyl, $C_5$ or $C_6$ alicyclic ring, benzene or substituted phenyl; the substituted phenyl is a phenyl with one to four substituents on the benzene ring, the substituent being halogen (preferably chloro), hydroxyl, alkyl (preferably $C_1$-$C_3$ alkyl and more preferably $C_1$-$C_3$ linear chain alkyl), nitro, alkoxy or amino; the $C_1$-$C_5$ alkyl (preferably $C_1$-$C_3$ alkyl) and the alkyl moiety in $C_1$-$C_4$ alkoxy, $C_1$-$C_4$ acyl and $C_5$ or $C_6$ alicyclic ring is preferably linear chain alkyl which can be optionally substituted by 1~3 fluorine atoms;

The asymmetric carbon atoms in the structure are achiral or chiral carbon atoms; For chiral carbon atoms, the configuration of $C_1$ and $C_2$ are respectively (1S,2R), (1S,2S), (1R,2S) or (1R,2R); wherein, the (1SR,2RS) isomer is an erythro isomer and (1SR,2SR) isomer is a threo isomer.

Where the compound of formula (1) is a free alkali, they can form various salts with various inorganic acids or organic acids.

In one embodiment, the salt is a salt containing a pharmaceutically acceptable anions, for example, hydrochloride, hydrobromide, hydriodide, nitrate, sulfate or hydrosulfate, phosphate or acid phosphate, acetate, lactate, citrate, tartrate, maleate, fumarate, gluconate, saccharate, benzoate, methanesulfonate, methanesulfonate, ethanesulfonate, benzene sulfonate or p-toluenesulfonate, and preferably hydrochloride, hydrobromide, sulfate, trifluoroacetate and methanesulfonate.

In another embodiment, the salt contains 0.5~4 molecules of crystal water.

Preferably, the 1-butyl-2-hydroxyl aralkyl piperazine derivatives are selected from the group consisting of:

VIII-1 (1SR,2RS)-N¹-p-methoxylphenyl-N⁴-[1-butyl-2-(5'-chloro-6'-methoxyl-2'-naphthyl)hydroxyethyl]piperazine, VIII-2 (1SR,2SR)-N¹-p-methoxylphenyl-N⁴-[1-butyl-2-(5'-chloro-6'-methoxyl-2'-naphthyl)hydroxyethyl]piperazine, VIII-3 (1SR,2RS)-N¹-o-methoxylphenyl-N⁴-[1-butyl-2-(5'-chloro-6'-methoxyl-2'-naphthyl)hydroxyethyl]piperazine, VIII-4 (1SR,2SR)-N¹-o-methoxylphenyl-N⁴-[1-butyl-2-(5'-chloro-6'-methoxyl-2'-naphthyl)hydroxyethyl]piperazine, VIII-5 (1SR,2RS)-N¹-m-chlorophenyl-N⁴-[1-butyl-2-(5'-chloro-6'-methoxyl-2'-naphthyl)hydroxyethyl]piperazine, VIII-6 (1SR,2SR)-N¹-m-chlorophenyl-N⁴-[1-butyl-2-(5'-chloro-6'-methoxyl-2'-naphthyl)hydroxyethyl]piperazine, VIII-7 (1SR,2RS)-N¹-(2,3-dimethylphenyl)-N⁴-[1-butyl-2-(5'-chloro-6'-methoxyl-2'-naphthyl)hydroxyethyl]piperazine, VIII-8 (1SR,2SR)-N¹-(2,3-dimethylphenyl)-N⁴-[1-butyl-2-(5'-chloro-6'-methoxyl-2'-naphthyl)hydroxyethyl]piperazine, VIII-9 (1SR,2RS)-N¹-benzyl-N⁴-[1-butyl-2-(5'-chloro-6'-methoxyl-2'-naphthyl)hydroxyethyl]piperazine, VIII-10 (1SR,2 SR)-N¹-benzyl-N⁴-[1-butyl-2-(5'-chloro-6'-methoxyl-2'-naphthyl) hydroxyethyl]piperazine, VIII-11 (1SR,2RS)-N¹-p-nitrobenzyl-N⁴-[1-butyl-2-(5'-chloro-6'-methoxyl-2'-naphthyl)hydroxyethyl]piperazine, VIII-12 (1SR,2 SR)-N¹-p-nitrobenzyl-N⁴-[1-butyl-2-(5'-chloro-6'-methoxyl-2'-naphthyl)hydroxyethyl]piperazine, VIII-13 (1SR,2RS)-N¹-p-aminolbenzyl-N⁴-[1-butyl-2-(5'-chloro-6'-methoxyl-2'-naphthyl)hydroxyethyl]piperazine, VIII-14 (1SR,2SR)-N¹-p-aminolbenzyl-N⁴-[1-butyl-2-(5'-chloro-6'-methoxyl-2'-naphthyl)hydroxyethyl]piperazine, VIII-15 (1SR,2RS)-N¹-(3',4',5'-trimethoxybenzyl)-N⁴-[1-butyl-2-(5'-chloro-6'-methoxyl-2'-naphthyl)hydroxyethyl]piperazine, VIII-16 (1SR,2SR)-N¹-(3',4',5'-trimethoxybenzyl)-N⁴-[1-butyl-2-(5'-chloro-6'-methoxyl-2'-naphthyl)hydroxyethyl]piperazine, VIII-17 (1SR,2RS)-N¹-α-phenemyl-N⁴-[1-butyl-2-(5'-chloro-6'-methoxyl-2'-naphthyl)hydroxyethyl]piperazine, VIII-18 (1SR,2SR)-N¹-α-phenemyl-N⁴-[1-butyl-2-(5'-chloro-6'-methoxyl-2'-naphthyl)hydroxyethyl]piperazine, VIII-19 (1SR,2RS)-N¹-benzhydryl-N⁴-[1-butyl-2-(5'-chloro-6'-methoxyl-2'-Naphthyl)hydroxyethyl]piperazine, VIII-20 (1SR,2SR)-N¹-benzhydryl-N⁴-[1-butyl-2-(5'-chloro-6'-methoxyl-2'-Naphthyl)hydroxyethyl]piperazine, VIII-21 (1SR,2RS)-N¹-cinnamyl-N⁴-[1-butyl-2-(5'-chloro-6'-methoxyl-2'-Naphthyl)hydroxyethyl]piperazine, VIII-22 (1SR,2SR)-N¹-cinnamyl-N⁴-[1-butyl-2-(5'-chloro-6'-methoxyl-2'-naphthyl)hydroxyethyl]piperazine, IX-23 (1S,2R)-N¹-benzyl-N⁴-[1-butyl-2-(5'-chloro-6'-methoxyl-2'-naphthyl) hydroxyethyl]piperazine, IX-24 (1S,2S)-N¹-benzyl-N⁴-[1-butyl-2-(5'-chloro-6'-methoxyl-2'-naphthyl)hydroxyethyl]piperazine, IX-25 (1R,2S)-N¹-benzyl-N⁴-[1-butyl-2-(5'-chloro-6'-methoxyl-2'-naphthyl)hydroxyethyl]piperazine, and IX-26 (1R,2R)-N¹-benzyl-N⁴-[1-butyl-2-(5'-chloro-6'-methoxyl-2'-naphthyl)hydroxyethyl]piperazine.

Most preferred are:

VIII-9 (1SR,2RS)-N¹-benzyl-N⁴-[1-butyl-2-(5'-chloro-6'-methoxyl-2'-naphthyl) hydroxyethyl]piperazine, VIII-10 (1SR,2SR)-N¹-benzyl-N⁴-[1-butyl-2-(5'-chloro-6'-methoxyl-2'-naphthyl) hydroxyethyl]piperazine, IX-23 (1S,2R)-N¹-benzyl-N⁴-[1-butyl-2-(5'-chloro-6'-methoxyl-2'-naphthyl) hydroxyethyl]piperazine, IX-24 (1S,2S)-N¹-benzyl-N⁴-[1-butyl-2-(5'-chloro-6'-methoxyl-2'-naphthyl) hydroxyethyl]piperazine, IX-25 (1R,2S)-N¹-benzyl-N⁴-[1-butyl-2-(5'-chloro-6'-methoxyl-2'-naphthyl) hydroxyethyl]piperazine, and IX-26 (1S,2R)-N¹-benzyl-N⁴-[1-butyl-2-(5'-chloro-6'-methoxyl-2'-naphthyl) hydroxyethyl]piperazine.

The structures of the compounds are shown in Table 1.

TABLE 1 the structures of the compounds

| Code | Configuration | Ar₁ | R₁ | m |
|---|---|---|---|---|
| VIII-1 | (1SR,2RS) | 4-OCH₃-C₆H₄ | H | 0 |
| VIII-2 | (1SR,2SR) | 4-OCH₃-C₆H₄ | H | 0 |
| VIII-3 | (1SR,2RS) | 2-OCH₃-C₆H₄ | H | 0 |
| VIII-4 | (1SR,2SR) | 2-OCH₃-C₆H₄ | H | 0 |
| VIII-5 | (1SR,2RS) | 3-Cl-C₆H₄ | H | 0 |
| VIII-6 | (1SR,2SR) | 3-Cl-C₆H₄ | H | 0 |
| VIII-7 | (1SR,2RS) | 2,6-(CH₃)₂-C₆H₃ | H | 0 |
| VIII-8 | (1SR,2SR) | 2,6-(CH₃)₂-C₆H₃ | H | 0 |
| VIII-9 | (1SR,2RS) | Ph | H | 1 |
| VIII-10 | (1SR,2SR) | Ph | H | 1 |

TABLE 1-continued the structures of the compounds

| Code | Configuration | Ar₁ | R₁ | m |
|---|---|---|---|---|
| VIII-11 | (1SR,2RS) | 4-NO₂-C₆H₄ | H | 1 |
| VIII-12 | (1SR,2SR) | 4-NO₂-C₆H₄ | H | 1 |
| VIII-13 | (1SR,2RS) | 4-NH₂-C₆H₄ | H | 1 |
| VIII-14 | (1SR,2SR) | 4-NH₂-C₆H₄ | H | 1 |
| VIII-15 | (1SR,2RS) | 3,4,5-(OCH₃)₃-C₆H₂ | H | 1 |
| VIII-16 | (1SR,2SR) | 3,4,5-(OCH₃)₃-C₆H₂ | H | 1 |
| VIII-17 | (1SR,2RS) | Ph | CH₃ | 1 |
| VIII-18 | (1SR,2SR) | Ph | CH₃ | 1 |
| VIII-19 | (1SR,2RS) | Ph | Ph | 1 |
| VIII-20 | (1SR,2SR) | Ph | Ph | 1 |
| VIII-21 | (1SR,2RS) | PhCH=CH- | H | 1 |
| VIII-22 | (1SR,2SR) | PhCH=CH- | H | 1 |
| IX-23 | (1S,2R) | Ph | H | 1 |
| IX-24 | (1S,2S) | Ph | H | 1 |
| IX-25 | (1R,2S) | Ph | H | 1 |
| IX-26 | (1R,2R) | Ph | H | 1 |

In one embodiment, the compounds of VIII-1~VIII-22, which are erythro or threo isomer, can be synthesized according to the method below:

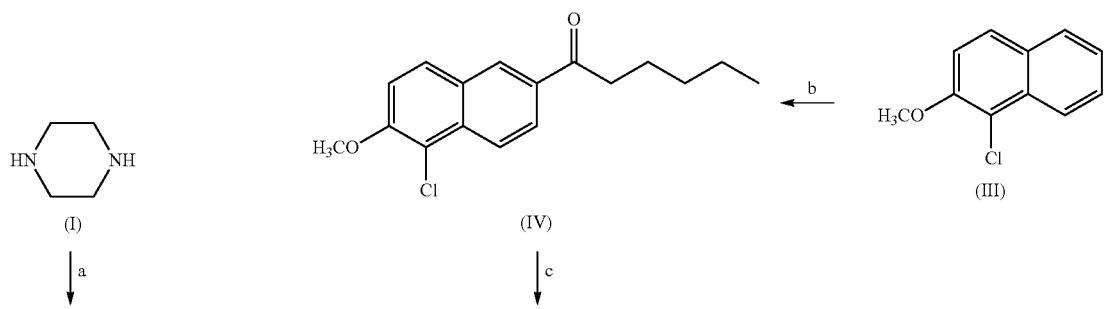

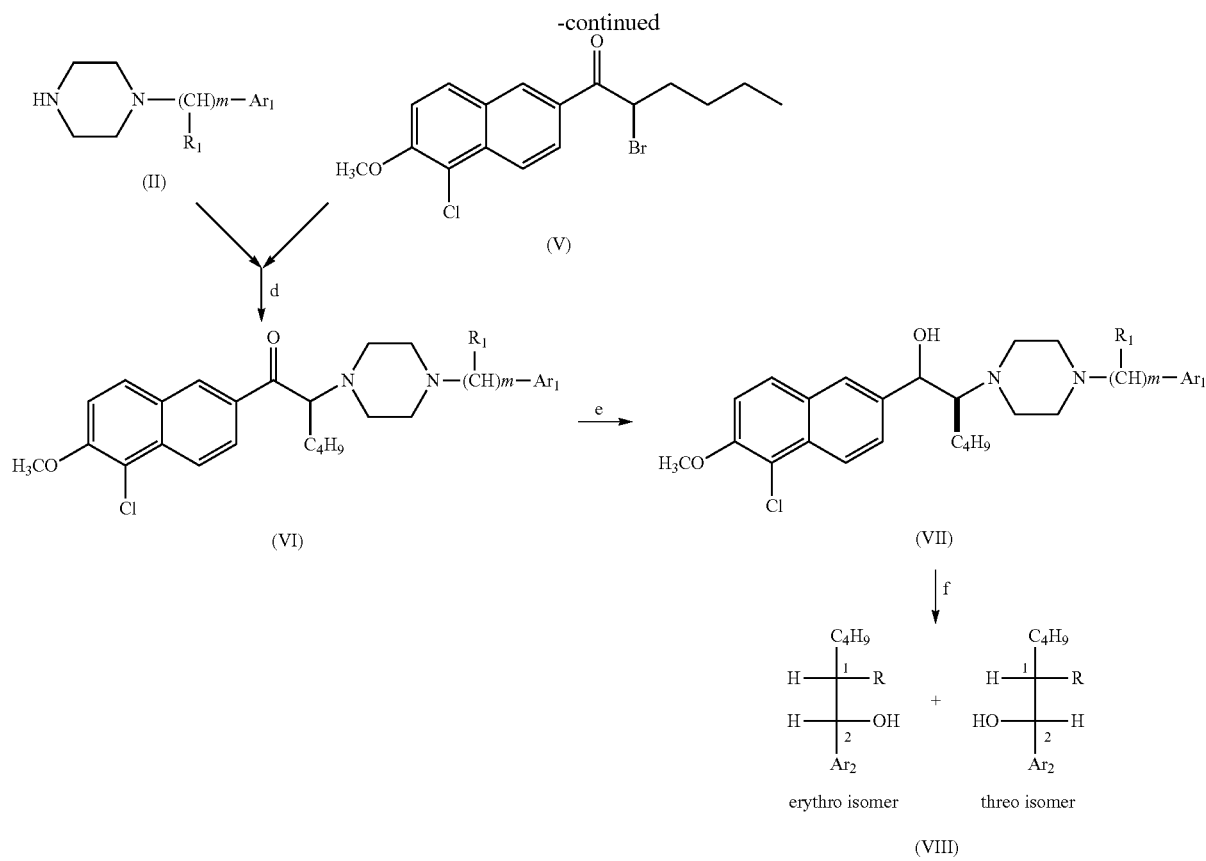

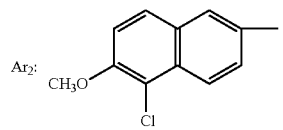

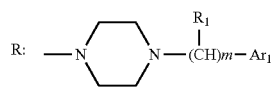

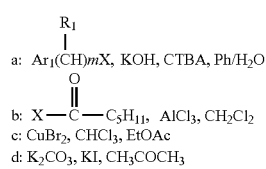

a: Ar$_1$(CH)$m$X, KOH, CTBA, Ph/H$_2$O
b: X—C(=O)—C$_5$H$_{11}$, AlCl$_3$, CH$_2$Cl$_2$
c: CuBr$_2$, CHCl$_3$, EtOAc
d: K$_2$CO$_3$, KI, CH$_3$COCH$_3$
e: NaBH$_4$, CH$_3$OH/Al(OiPr)$_3$, i-PrOH
f: separation piperazine is used as the starting material. Firstly a nucleophilic substitution reaction with a corresponding halogenated arylalkane is performed to obtain N-monoalkylated compound (II). This reaction is carried out under phase transfer catalytic condition. N-monoalkylation of piperazine may be carried out by reaction with KOH in a reaction media of benzene/water using cetyl trimethylammonium bromide (CTAB) as the phase transfer catalyst, and the yield may be up to 86%. The phase transfer catalyst is the catalyst as reported in Chinese patent ZL02111934.1.

Compound (III) is reacted with corresponding acyl chloride to carry out a Friedel-Crafts reaction to obtain aryl alkanone (IV). This reaction is performed at room temperature, using dichloromethane as the solvent and anhydrous aluminum chloride as the catalyst. The yield is about 80%.

Compound (IV) is bromized to give halogenated aryl alkanone (V). This reaction is performed by heating under refluxing, using CuBr$_2$ as brominating agent and a mixed solution of chloroform and ethyl acetate as the solvent. The yield is about 85%.

Compound (II) can be reacted with compound (V) to conduct N$^4$-alkylation reaction, thereby providing aryl alkanone piperazine compound (VI). The reaction is performed under refluxing for 8-24 hours using K$_2$CO$_3$/acetone as reaction system. The yield is 80%.

Compound (VI) is reacted with NaBH$_4$ in methanol at room temperature for 0.5-1 hours, or with aluminium isopropoxide in isopropanol at 60-65° C. for 24-48 hours, to reduce carbonyl group, thereby obtaining corresponding aryl alkanol piperazine compound (VII).

The compound (VII) is separated by column chromatography, and the erythro and threo isomers (VIII) of corresponding 1-butyl-2-hydroxyl aralkyl piperazine derivatives are obtained. Compounds VIII-1~VIII22 of interest can be obtained using the procedures above.

Haloarylalkane compounds in step a, and acyl chloride compound and Compound III in step b are all commercial available, or can be prepared by the conventional methods reported in literatures.

For the optical isomers of Compounds IX-23~IX-26, they can be synthesized by the method below:

Compound 3 is obtained by starting from chiral norleucine 1, protecting amino group with phthaloyl and acylating carboxyl group with oxalyl chloride; then Compound 3 is reacted with Compound 4 to carry out Friedel-Crafts reaction, thereby obtaining compound 5. Compound 5 is reduced by aluminium isopropoxide, and then hydrolyzed to obtain Compound 7. Compound 7 is condensed with Compound 8 to obtain Compound 9, then the optical pure product of interest (IX) is obtained by column chromatography separation. The detailed synthesis scheme is shown as below:

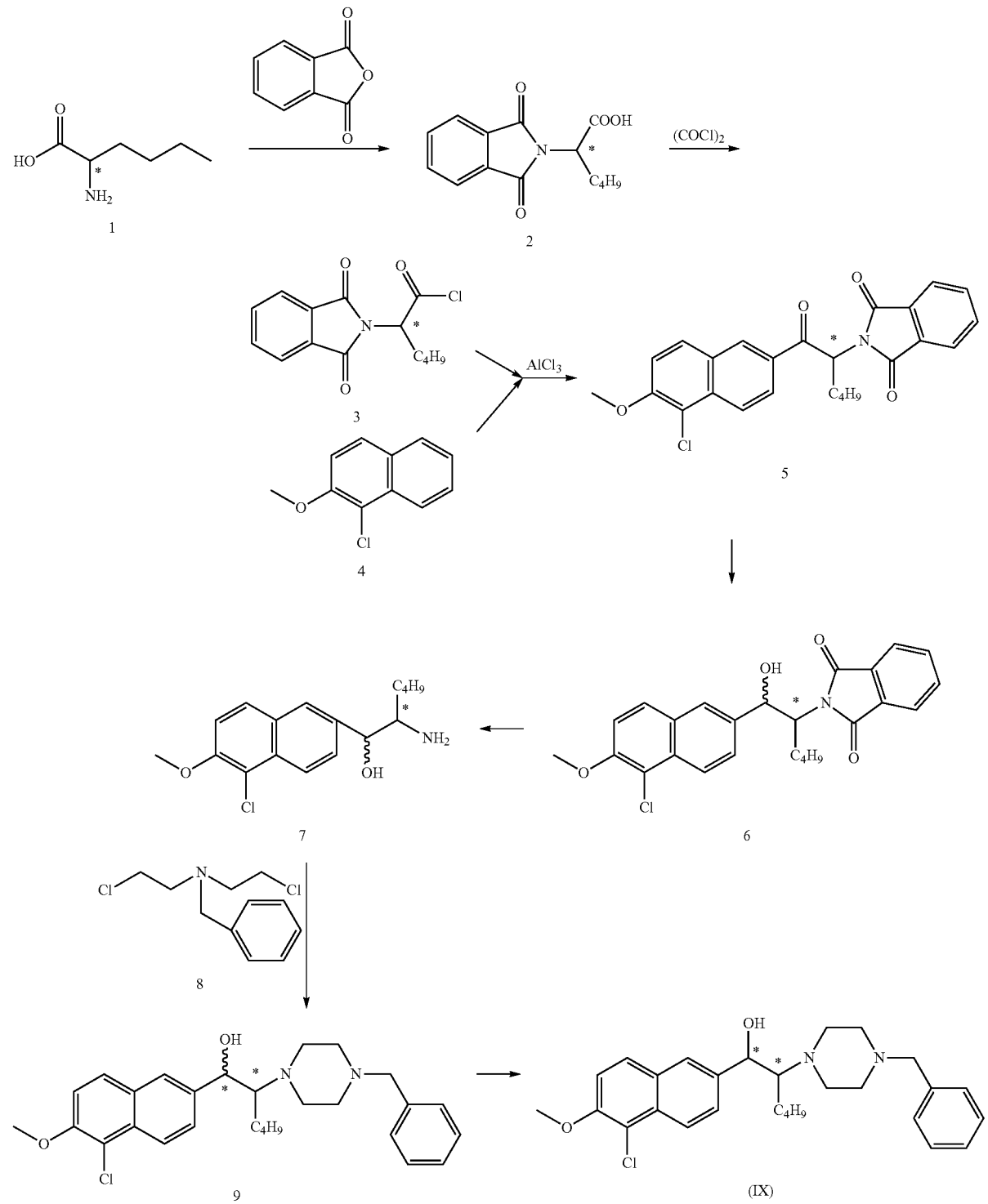

The present invention uses the prochiral method to synthesize the four optical isomers of compound $N^1$-benzyl-$N^4$-[1-butyl-2-(5'-chloro-6'-methoxyl-2'-naphthyl) hydroxyethyl] piperazine:

A mixture of (1S,2R) isomer and (1S,2S) isomer is synthesized using L-norleucine as starting material, then separated by column chromatography with silica gel or alumina as carrier and the solution of methylene chloride and methanol with a volume ratio of 200:1 as eluant, to obtain (1S,2S)-$N^1$-benzyl-$N^4$-[1-butyl-2-(5'-chloro-6'-methoxyl-2'-naphthyl) hydroxyethyl]piperazine (IX-24) and (1S,2R)-$N^1$-benzyl-$N^4$-[1-butyl-2-(5'-chloro-6'-methoxyl-2'-naphthyl) hydroxyethyl]piperazine (IX-23). If D-norleucine is used as starting material, according to the same method, (1S,2S)-$N^1$-benzyl-$N^4$-[1-butyl-2-(5'-chloro-6'-methoxyl-2'-naphthyl) hydroxy ethyl]piperazine (IX-25) and (1S,2R)-$N^1$-benzyl-$N^4$-[1-butyl-2-(5'-chloro-6'-methoxyl-2'-naphthyl) hydroxyethyl]piperazine (IX-26) are obtained.

For the synthesis method above, the materials are available, the products need not resolution and are obtained with a high optical purity and a high overall yield. The purity of four optical isomers are determined by high performance liquid chromatography with a chiral column, and enantiomeric excess (ee) thereof are all more than 99%. [Detective condition: OJ-H chiral column (from Daicel industries. Co. Ltd., JP) 4.6×250 mm; mobile phase: n-hexane:ethanol:diethylamine=40:60:0.1 (v/v/v): ultraviolet wavelength: UV220 nm; column temperature: 35° C.]

The configurations of the four optical isomers can be presumed by the configuration of the starting material and the coupling constant of the product. In the course of reaction, the bonds connecting to the chiral center do not break and the relative size of the groups connected do not change, therefore, the configuration of C1 connecting to N in the final product is the same as that of the starting material norleucine. Furthermore, the configuration of C2 can be presumed by the coupling constant between Hα and Hβ connecting to the chiral center. Specifically, the lower coupling constant Jαβ represents erythro form, and corresponding configuration of which is (1S,2R) or (1R,2S); the higher coupling constant Jαβ represents threo form, and corresponding configuration thereof is (1S,2S) or (1R,2R). The detail is shown in table 2.

The (1S,2R) and (1S,2S) isomers are prepared using L-norleucine as the starting material; and the (1R,2S) and (1R,2R) isomers are prepared using D-norleucine as the starting material.

Monoamine transmitter reuptake inhibition experiment in vitro shows that the 1-butyl-2-hydroxyl aralkyl piperazine derivatives and the optical isomers thereof of the present invention are triple reuptake inhibitors, which has quite strong inhibition effect in vitro on the reuptake of monoamine transmitters DA, NE and 5-HT. The preferred compound VIII-10 has an equivalent in vitro inhibition effect on the reuptake for 5-HT and NA as compared with venlafaxine and SIPIyy24, and has a stronger inhibition activity on the reuptake for DA as compared with venlafaxine, SIPIyy24 and SIPI5286; Compound VIII-9 had a stronger inhibition activity on the reuptake of all the three monoamine transmitters as compared with venlafaxine, SIPIyy24 and SIPI5286.

In vivo antidepression activity studies in animals shows that: Compound VIII-9 has an equivalent in vivo antidepression activity as compared with venlafaxine and SIPI5286, and has a significant difference compared with the blank group; and the antidepression activity in vivo of Compound VIII-10 is stronger than that of venlafaxine and SIPI5286.

Acute toxicity study shows that $LD_{50}$ (95% confidence limit) of the preferred compound VIII-10 is 1048.5 (751.33~1433.7) mg/kg, MLD (minimum lethal dosage) of VIII-9 is more than 2844.7 mg/kg. Their acute toxicity are less than that of SIPIyy24 (a preferred compound in China Patent ZL02111934.1) and SIPI5286 (a preferred compound in Chinese patent ZL200510030354.1)

Pharmacokinetics study shows that half life of Compound VIII-10 oral administrated is 16.41 hours, which is longer than that of VIII-9 (5.89 hours) and SIPI5286 (5.71 hours). The bioavailability of Compound VIII-10 oral administrated is 63.78%, which is higher than that of VIII-9 (16.32%) and SIPI5286 (51.63%). Therefore, Compound VIII-10 is of good druggability.

The 1-butyl-2-hydroxyl aralkyl piperazine derivatives of the present invention have triple inhibition effect on reuptake of 5-HT, NA and DA, and can be used to prepare antidepressants.

The derivatives of the present invention can be administrated to patients in need thereof in the form of composition by the route of oral administration, injection and the like.

The present invention also relates to a method for treating a patient with depression, comprising administering a therapeutically effective amount of derivatives of the invention or the composition containing the same to the patient. The administration route may be oral administration or injection.

TABLE 2 the configurations presumed of the four optical isomers

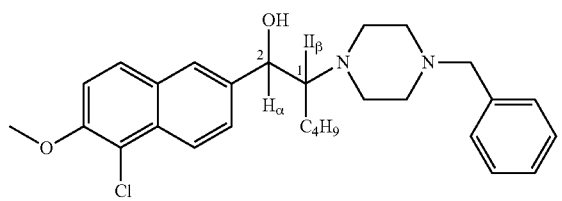

| compound | configuration of norleucine | configuration of $C_1$ | coupling constant $J_{αβ}$/Hz | Erythro/Threo | configuration of $C_2$ | configuration of product |
|---|---|---|---|---|---|---|
| IX-23 | L | S | 2.0 | Erythro | R | 1S, 2R |
| IX-24 | L | S | 9.6 | Threo | S | 1S, 2S |
| IX-25 | D | R | 2.0 | Erythro | S | 1R, 2S |
| IX-26 | D | R | 9.6 | Threo | R | 1R, 2R |

The composition contains therapeutically effective amount of derivatives of the present invention as active ingredient, together with one or more pharmaceutically acceptable carriers.

The carrier means conventional carriers in pharmaceutical field, for example, diluents, excipients such as water; adhesive such as cellulose derivatives, gelatin, polyvinylpyrrolidone and the like; fillers such as starch and the like; disintegrating agents such as calcium carbonate, sodium bicarbonate and the like; in addition, other adjuvants such as flavoring agents and sweeteners may be added into the composition.

For oral administration, it may be formulated into conventional solid preparations such as tablet, powder or capsule; for injection administration, it may be formulated into injection solution.

Various preparations of the composition according to the present invention can be prepared using conventional methods in pharmaceutical field, wherein the content of active ingredient is 0.1% to 99.5% (by weight).

The amount administrated in the present invention may vary according to route of administration, age and weight of the patient, type and severity of the disease being treated, and the like, and the daily dose is 5-30 mg/kg body weight (oral) or 1-10 mg/kg body weight (injection). The derivatives of the present invention showed antagonism against depression in animal trials.

In order to overcome the defect of SIPI5286, structure modification is carried out using SIPI5286 as the lead compound. The present inventor found that, when the substituent group of C1 is fatty hydrocarbon, with the increase of carbon chain from 1 to 4, the erythro and threo isomers of the compounds show better inhibition on reuptake of 5-HT, NA and DA, comparable with SIPIyy24 and the positive control venlafaxine. When the substituent is butyl, that is 1-butyl-2-hydroxyl aralkyl piperazine derivatives of the present invention, the inhibition activity on reuptake of 5-HT, NA and DA of the erythro and threo isomers thereof reach the maximum, higher than that of SIPIyy24, SIPI5286 and the positive control venlafaxine. However, when the substituent of C1 is pentyl, the inhibition activity decreases sharply. When structure qualification was carried out on other compounds in ZL02111934.1, the present inventor found that when the substituent of C1 is butyl, the inhibition activity on reuptake of 5-HT, NA and DA reached the maximum value for all. Therefore, the present inventor considered that 1-butyl-2-hydroxyl aralkyl piperazine derivatives have the strongest activity in the aryl alkanol piperazine derivatives.

The subsequent in vivo study on animals also shows that, compared with aryl alkanol piperazine derivatives disclosed in Chinese patent ZL02111934.1 and the optical isomer disclosed in Chinese patent ZL200510030354.1, the 1-butyl-2-hydroxyl aralkyl piperazine derivatives of the present invention have advantages in stronger activity in antidepression, lower toxicity, higher bioavailability, longer half life and better druggablity.

In conclusion, the 1-butyl-2-hydroxyl aralkyl piperazine derivatives in the present invention, compared with current clinically used dual targets depressants (for example, venlafaxine) may have stronger potency, broader indications, lower toxicity and less neurotoxic side reactions. The derivatives have the advantages of stronger activity in antidepression, lower toxicity, higher bioavailability, longer half life and better druggablity, compared with aryl alkanol piperazine derivatives disclosed in Chinese patent ZL02111934.1 and optical isomers disclosed in Chinese patent ZL200510030354.1.

SPECIFIC MODES FOR CARRYING OUT THE INVENTION

General Method 1
Synthesis of N-Aralkyl Piperazine Hydrochloride (II)

Piperazine hexahydrate (350 mmol, from Shanghai chemical reagent station), solid KOH (100 mmol) and CTAB (Hexadecyl Trimethylammonium Bromide, 1 mmol) were added to 18 ml water and heated to dissolve. 140 ml solution of aralkyl chloride (100 mmol, commercial available) in benzene was added dropwise at the temperature of 70° C. After dropping the reactant was refluxed for 1.5 hours, and allowed to stand and demix, then the organic phase was washed with 50 ml water and 50 ml saturated NaCl solution respectively, dried with $MgSO_4$ and filtered. The solvent was evaporated to dryness under reduced pressure, and the concentrate was then dissolved in 50 ml absolute alcohol and adjusted to pH of 3 by dropping the solution of $HCl/C_2H_5OH$. Then solid precipitated and was filtered and dried. N-aralkyl piperazine hydrochloride was obtained by recrystallization in ethanol. The yield was 80%-86%.

General Method 2
Synthesis of 2-hexanone-5-chloro-6-methoxylnaphthaline (IV)

Compound (III) (28.4 mmol) was dissolved in dichloromethane (30 ml). $AlCl_3$ (30.8 mmol) was added, the reactant was stirred for 1 hour at room temperature. With $AlCl_3$ dissolving gradually, the color of the solution became darker to light brown. Hexanoyl chloride (23.7 mmol) was added dropwise slowly to the mixture, with the temperature controlled below 10° C. After dropping, the reactant was warmed naturally to room temperature and stirred for 1 h. The color of the reaction solution became darker to brown. The reaction solution was poured into a mixture of hydrochloric acid (20 ml)/crashed ice (50 g) under stirring, and the color of organic phase turned lighter to be light yellow to yellow. The organic phase was separated, washed with water (20 ml×3) till the aqueous phase being neutral and dried with anhydrous $Na_2SO_4$ overnight. The desiccant was filtered, the residue was washed with a small amount of dichloromethane. Then the solvent of the filtrate was evaporated, and light yellow oily substance was obtained. The product IV was separated as a light yellow oily product by column chromatography (ethyl acetate:petroleum ether=1:400~1:60), allowed to stand and solidified. The yield was about 80%.

General Method 3
Synthesis of 2-(α-bromo-hexanone)-5-chloro-6-methoxyl-naphthaline (V)

Compound (IV) (21 mmol) was dissolved in the mixture of ethyl acetate (50 ml) and chloroform (50 ml), then $CuBr_2$ (40.2 mmol) was added, the reaction was performed under refluxing for 3 hours. CuBr produced was filtered. The filtrate was washed with water (20 ml×3), and dried with anhydrous $Na_2SO_4$ overnight. The desiccant was filtered, with the residue washed with a small amount of ethyl acetate. The solvent of the filtrate was evaporated. Light yellow crystalline solid was obtained by recrystallization with ethanol. The yield was about 85%.

General Method 4
Synthesis of $N^1$-aralkyl-$N^4$-[1-(5'-chloro-6'-methoxyl-2'-naphthoyl)pentyl]piperazine hydrochloride (VI)

N-aralkyl piperazine hydrochloride (II) (10 mmol), 2-(α-bromo-hexanone)-5-chloro-6-methoxylnaphthaline (V) (12 mmol), potassium iodide (1 mmol) and anhydrous $K_2CO_3$ (35 mmol) were placed into acetone (50 ml). The reaction was performed by stirring under refluxing for 8 to 12 hours. After filtered, the solvent was evaporated to dryness under reduced pressure. 50 ml water was added, the reactant was extracted with EtOAc (100 ml×3). The ester layers were pooled and washed with 20 ml water and 30 ml saturated NaCl solution successively, then dried with $MgSO_4$. After filtration, the solvent was evaporated. The concentrate was dissolved by adding 30 ml of ethanol, and adjusted to a pH of 2 with $HCl/C_2H_5OH$ (5N). The precipitated solid was filtered and recrystallized in ethanol/water or methanol to obtain Compound (VI) in a yield of 60%-85%.

General Method 5

Synthesis of $N^1$-aralkyl-$N^4$-[1-butyl-2-(5'-chloro-6'-methoxyl-2'-naphthyl)hydroxyethyl]piperazine hydrochloride (VII)

Aluminium isopropoxide (35 mmol) was dissolved in 80 ml of isopropanol, and anhydrous $AlCl_3$ (3.5 mmol) was added. After heated to 45-50° C., the mixture was stirred for 30 min until clear, the solution of $N^1$-aralkyl-$N^4$-aralkylacyl alkylpiperazine (10 mmol) in isopropanol was added. The temperature was increased to 60-65° C., the reaction was performed until the material spot disappeared (TLC detected, 6-48 hours). Then, 15% of NaOH solution (by weight) was added to adjust to a pH of about 7. Extraction was performed with dichloromethane or ethyl acetate and the extract was washed with saturated NaCl solution (20 ml), dried with $MgSO_4$. After filtration, the solvent of filtrate was evaporated under reduced pressure. The residue was dissolved in 20 ml of ethanol, and adjusted to a pH of 2 with $HCl/C_2H_5OH$. The solid precipitated and was filtered in a yield of 85%~95%.

EXAMPLE 1

VIII-1 (1SR,2RS)-$N^1$-p-methoxylphenyl-$N^4$-[1-butyl-2-(5'-chloro-6'-methoxyl-2'-naphthyl)hydroxyethyl]piperazine (erythro form)

4.2 g of $N^1$-p-methoxylphenyl-$N^4$-[1-butyl-2-carbonyl-2-(5-chloro-6-methoxy naphthalene-2-yl)]ethylpiperazine hydrochloride was synthesized using $N^1$-p-methoxylphenylpiperazine (10 mmol) and 2-(α-bromo-hexanone)-5-chloro-6-methoxylnaphthaline (10 mmol), according to general method 2 to general method 4, in a yield of 79%, m.p=231.5-233.6° C. (dec). Then the reduction of carbonyl was performed upon $N^1$-p-methoxylphenyl-$N^4$-[1-butyl-2-carbonyl-2-(5-chloro-6-methoxy naphthalene-2-yl)]ethylpiperazine according to general method 5, and 3.78 g of $N^1$-p-methoxylphenyl-$N^4$-[1-butyl-2-hydroxy-2-(5-chloro-6-methoxynaphthalene-2-yl)]ethylpiperazine hydrochloride was obtained in a yield of 90%. The compound produced was transformed to free alkali thereof and separated by column chromatography to obtain the erythro form, then was dissolved in ethanol, and adjusted to a pH of 2 with $HCl/C_2H_5OH$(5N). The precipitated solid was filtered, and compound (VIII-1) was obtained by recrystallization in ethanol/water or methanol. Element analysis of the compound showed that 0.5 molecule of crystal water was contained in the compound.

m.p=221.6-223.2° C. (dec). MS: m/z 483 ($M^+$).
$^1$HNMR (DMSO-d6): δ 0.73-1.66 (m, 9H, $CH_2CH_2CH_2CH_3$), 2.65-2.91 (m, 9H, CH+piperazine-H), 3.76 (s, 3H, $OCH_3$), 3.87 (s, 3H, $OCH_3$), 5.0 (d, 1H, CH, J=4.0), 5.17 (d, 1H, OH), 6.84-8.04 (m, 9H, Ar—H)

EXAMPLE 2

VIII-2 (1SR,2SR)-$N^1$-p-methoxylphenyl-$N^4$-[1-butyl-2-(5'-chloro-6'-methoxyl-2'-naphthyl)hydroxyethyl]piperazine (threo form)

4.2 g of $N^1$-p-methoxylphenyl-$N^4$-[1-butyl-2-carbonyl-2-(5-chloro-6-methoxy naphthalene-2-yl)]ethylpiperazine hydrochloride was synthesized using $N^1$-p-methoxylphenylpiperazine (10 mmol) and 2-(α-bromo-hexanone)-5-chloro-6-methoxylnaphthaline (10 mmol), according to general method 2 to general method 4, in a yield of 79%, m.p=231.5-233.6° C. (dec). Then the reduction of carbonyl was performed upon $N^1$-p-methoxylphenyl-$N^4$-[1-butyl-2-carbonyl-2-(5-chloro-6-methoxy naphthalene-2-yl)]ethylpiperazine according to general method 5, and 3.78 g of $N^1$-p-methoxylphenyl-$N^4$-[1-butyl-2-hydroxy-2-(5-chloro-6-methoxynaphthalene-2-yl)]ethylpiperazine hydrochloride was obtained in a yield of 90%. The compound produced was transformed to free alkali thereof and separated by column chromatography. The threo form was obtained and dissolved in ethanol, and adjusted to a pH of 2 with $HCl/C_2H_5OH$(5N). The precipitated solid was filtered, and Compound VIII-2 was obtained by recrystallization in ethanol/water or methanol. Element analysis of the compound showed that 2 molecules of crystal water were contained in the compound.

m.p=220.4-222.8° C. (dec). MS: m/z 483 ($M^+$)
$^1$HNMR (DMSO-d6): δ 0.65-1.51 (m, 9H, $CH_2CH_2CH_2CH_3$), 2.49-2.97 (m, 9H, CH+piperazine-H), 3.78 (s, 3H, $OCH_3$), 3.87 (s, 3H, $OCH_3$), 4.6 (d, 1H, CH, J=8.0), 5.14 (d, 1H, OH), 6.86-8.06 (m, 9H, Ar—H).

EXAMPLE 3

VIII-3 (1SR,2RS)-$N^1$-o-methoxylphenyl-$N^4$-[1-butyl-2-(5'-chloro-6'-methoxyl-2'-naphthyl)hydroxyethyl]piperazine (erythro form)

4.03 g of $N^1$-o-methoxylphenyl-$N^4$-[1-butyl-2-carbonyl-2-(5-chloro-6-methoxy naphthalene-2-yl)]ethylpiperazine hydrochloride was synthesized using $N^1$-o-methoxylphenylpiperazine (10 mmol) and 2-(α-bromo-hexanone)-5-chloro-6-methoxylnaphthaline (10 mmol), according to general method 2 to general method 4, in a yield of 78%, m.p=232.4-234.1° C. (dec).

Then the reduction of carbonyl was performed upon $N^1$-o-methoxylphenyl-$N^4$-[1-butyl-2-carbonyl-2-(5-chloro-6-methoxy naphthalene-2-yl)]ethylpiperazine according to general method 5, and 3.58 g of $N^1$-o-methoxylphenyl-$N^4$-[1-butyl-2-hydroxy-2-(5-chloro-6-methoxynaphthalene-2-yl)]ethylpiperazine hydrochloride was obtained in a yield of 89%. The compound produced was transformed to free alkali thereof and separated by column chromatography. The erythro form was obtained and dissolved in ethanol, and adjusted to a pH of 2 with $HCl/C_2H_5OH$(5N). The precipitated solid was filtered, and Compound VIII-3 was obtained by recrystallization in ethanol/water or methanol. Element analysis of the compound showed that 2 molecules of crystal water were contained in the compound.

m.p=227.3-229.1° C. (dec). MS: m/z 483 ($M^+$).
$^1$HNMR (DMSO-d6): δ 0.73-1.66 (m, 9H, $CH_2CH_2CH_2CH_3$), 2.65-2.91 (m, 9H, CH+ piperazine-H), 3.76 (s, 3H, $OCH_3$), 3.98 (s, 3H, $OCH_3$), 5.0 (d, 1H, CH, J=4.0), 5.17 (d, 1H, OH), 6.84-8.04 (m, 9H, Ar—H)

EXAMPLE 4

VIII-4 (1SR,2SR)-$N^1$-o-methoxylphenyl-$N^4$-[1-butyl-2-(5'-chloro-6'-methoxyl-2'-naphthyl)hydroxyethyl]piperazine (threo form)

4.03 g of $N^1$-o-methoxylphenyl-$N^4$-[1-butyl-2-carbonyl-2-(5-chloro-6-methoxy naphthalene-2-yl)]ethylpiperazine hydrochloride was synthesized using $N^1$-o-methoxylphenylpiperazine (10 mmol) and 2-(α-bromo-hexanone)-5- chloro-6-methoxylnaphthaline (10 mmol), according to general method 2 to general method 4, in a yield of 78%, m.p=232.4-234.1° C. (dec).

Then the reduction of carbonyl was performed upon $N^1$-o-methoxylphenyl-$N^4$-[1-butyl-2-carbonyl-2-(5-chloro-6-methoxy naphthalene-2-yl)]ethylpiperazine according to general method 5, and 3.58 g of $N^1$-o-methoxylphenyl-$N^4$-[1-butyl-2-hydroxy-2-(5-chloro-6-methoxynaphthalene-2-yl)]ethylpiperazine hydrochloride was obtained in a yield of 89%. The compound produced was transformed to free alkali thereof and separated by column chromatography. The threo form was obtained and dissolved in ethanol, and adjusted to a pH of 2 with $HCl/C_2H_5OH$(5N). The precipitated solid was filtered, and Compound VIII-4 was obtained by recrystallization in ethanol/water or methanol. Element analysis of the compound showed that 2 molecules of crystal water were contained in the compound.

m.p=223.5-225.0° C. (dec). MS: m/z 483 ($M^+$).
$^1$HNMR (DMSO-d6): δ 0.65-1.51 (m, 9H, $CH_2CH_2CH_2CH_3$), 2.49-2.97 (m, 9H, CH+ piperazine-H), 3.78 (s, 3H, $OCH_3$), 3.98 (s, 3H, $OCH_3$), 4.6 (d, 1H, CH, J=8.0), 5.14 (d, 1H, OH), 6.86-8.06 (m, 9H, Ar—H).

EXAMPLE 5

VIII-5 (1SR,2RS)-$N^1$-m-chlorophenyl-$N^4$-[1-butyl-2-(5'-chloro-6'-methoxyl-2'-naphthyl)hydroxyethyl]piperazine (erythro form)

4.20 g of $N^1$-m-chlorophenyl-$N^4$-[1-butyl-2-carbonyl-2-(5-chloro-6-methoxy naphthalene-2-yl)]ethylpiperazine hydrochloride was synthesized using $N^1$-m-chlorophenylpiperazine (10 mmol) and 2-(α-bromo-hexanone)-5-chloro-6-methoxylnaphthaline (10 mmol), according to general method 2 to general method 4, in a yield of 79%, m.p=231.5-233.6° C. (dec).

Then the reduction of carbonyl was performed upon $N^1$-m-chlorophenyl-$N^4$-[1-butyl-2-carbonyl-2-(5-chloro-6-methoxy naphthalene-2-yl)]ethylpiperazine according to general method 5, and 3.78 g of $N^1$-m-chlorophenyl-$N^4$-[1-butyl-2-hydroxy-2-(5-chloro-6-methoxynaphthalene-2-yl)]ethylpiperazine hydrochloride was obtained in a yield of 90%. The compound produced was transformed to free alkali thereof and separated by column chromatography. The erythro form was obtained, and then dissolved in ethanol, and adjusted to a pH of 2 with $HCl/C_2H_5OH$(5N). The precipitated solid was filtered, and Compound VIII-5 was obtained by recrystallization in ethanol/water or methanol.

m.p=224.2-226.8° C. (dec). MS: m/z 487 ($M^+$).
$^1$HNMR (DMSO-d6): δ 0.73-1.66 (m, 9H, $CH_2CH_2CH_2CH_3$), 2.65-2.91 (m, 9H, CH+ piperazine-H), 3.76 (s, 3H, $OCH_3$), 5.0 (d, 1H, CH, J=4.0), 5.17 (d, 1H, OH), 6.84-8.04 (m, 9H, Ar—H)

EXAMPLE 6

VIII-6 (1SR,2SR)-$N^1$-m-chlorophenyl-$N^4$-[1-butyl-2-(5'-chloro-6'-methoxyl-2'-naphthyl)hydroxyethyl]piperazine (threo form)

4.20 g of $N^1$-m-chlorophenyl-$N^4$-[1-butyl-2-carbonyl-2-(5-chloro-6-methoxy naphthalene-2-yl)]ethylpiperazine hydrochloride was synthesized using $N^1$-m-chlorophenylpiperazine (10 mmol) and 2-(α-bromo-hexanone)-5-chloro-6-methoxylnaphthaline (10 mmol) according to general method 2 to general method 4, in a yield of 79%, m.p=231.5-233.6° C. (dec).

Then the reduction of carbonyl was performed upon $N^1$-m-chlorophenyl-$N^4$-[1-butyl-2-carbonyl-2-(5-chloro-6-methoxynaphthalene-2-yl)]ethylpiperazine according to general method 5, and 3.78 g of $N^1$-m-chlorophenyl-$N^4$-[1-butyl-2-hydroxy-2-(5-chloro-6-methoxynaphthalene-2-yl)]ethylpiperazine hydrochloride was obtained in a yield of 90%. The compound produced was transformed to free alkali thereof and separated by column chromatography. The threo form was obtained and dissolved in ethanol, and adjusted to a pH of 2 with $HCl/C_2H_5OH$ (5N). The precipitated solid was filtered, and Compound VIII-6 was obtained by recrystallization in ethanol/water or methanol.

m.p=220.4-222.8° C. (dec). MS: m/z 487 ($M^+$).
$^1$HNMR (DMSO-d6): δ 0.65-1.51 (m, 9H, $CH_2CH_2CH_2CH_3$), 2.49-2.97 (m, 9H, CH+ piperazine-H), 3.78 (s, 3H, $OCH_3$), 4.6 (d, 1H, CH, J=8.0), 5.14 (d, 1H, OH), 6.86-8.06 (m, 9H, Ar—H).

EXAMPLE 7

VIII-7 (1SR,2RS)-$N^1$-(2,3-dimethylphenyl)-$N^4$-[1-butyl-2-(5'-chloro-6'-methoxyl-2'-naphthyl)hydroxyethyl]piperazine (erythro form)

3.80 g of $N^1$-(2,3-dimethylphenyl)-$N^4$-[1-butyl-2-carbonyl-2-(5-chloro-6-methoxynaphthalene-2-yl)]ethylpiperazine hydrochloride was synthesized using $N^1$-(2,3-dimethylphenyl)piperazine (10 mmol) and 2-(α-bromo-hexanone)-5-chloro-6-methoxylnaphthaline (10 mmol), according to general method 2 to general method 4, in a yield of 80%, m.p=232.5-235.6° C. (dec).

Then the reduction of carbonyl was performed upon $N^1$-(2,3-dimethylphenyl)-$N^4$-[1-butyl-2-carbonyl-2-(5-chloro-6-methoxynaphthalene-2-yl(]ethylpiperazine according to general method 5, and 3.34 g of $N^1$-(2,3-dimethylphenyl)-$N^4$-[1-butyl-2-hydroxy-2-(5-chloro-6-methoxynaphthalene-2-yl)]ethylpiperazine hydrochloride was obtained in a yield of 88%. The compound produced was transformed to free alkali thereof and separated by column chromatography. The erythro form was obtained and dissolved in ethanol, and adjusted to a pH of 2 with $HCl/C_2H_5OH$(5N). The precipitated solid was filtered, and Compound VIII-7 was obtained by recrystallization in ethanol/water or methanol.

m.p=218.5-220.8° C. (dec). MS: m/z 481 ($M^+$).
$^1$HNMR (DMSO-d6): δ 0.74-0.77 (m, 3H, $CH_2CH_2CH_3$), 1.13-2.11 (m, 6H, $CH_2CH_2CH_3$), 2.15 (s, 3H, $CH_3$), 2.20 (s, 3H, $CH_3$), 2.50-2.87 (m, 9H, piperazine —CH), 3.99 (s, 3H, $OCH_3$), 5.06-5.07 (m, 1H, CH, J=4.0), 5.18-5.19 (d, 1H, OH), 6.83-8.05 (m, 8H, Ar—H).

EXAMPLE 8

VIII-8 (1SR,2SR)-$N^1$-(2,3-dimethylphenyl)-$N^4$-[1-butyl-2-(5'-chloro-6'-methoxyl-2'-naphthyl)hydroxyethyl]piperazine (threo form)

3.80 g of $N^1$-(2,3-dimethylphenyl)-$N^4$-[1-butyl-2-carbonyl-2-(5-chloro-6-methoxy naphthalene-2-yl)]ethylpiperazine hydrochloride was synthesized using $N^1$-(2,3-dimethylphenyl)piperazine (10 mmol) and 2-(α-bromo-hexanone)-5-chloro-6-methoxylnaphthaline (10 mmol), according to general method 2 to general method 4, in a yield of 80%, m.p=232.5-235.6° C. (dec).

Then the reduction of carbonyl was performed upon $N^1$-(2,3-dimethylphenyl)-$N^4$-[1-butyl-2-carbonyl-2-(5-chloro-6-methoxy naphthalene-2-yl)]ethylpiperazine according to general method 5, and 3.34 g of $N^1$-(2,3-dimethylphenyl)-$N^4$-

[1-butyl-2-hydroxy-2-(5-chloro-6-methoxy naphthalene-2-yl)]ethylpiperazine hydrochloride was obtained in a yield of 88%. The compound produced was transformed to free alkali thereof and separated by column chromatography. The threo form was obtained and dissolved in ethanol, and adjusted to a pH of 2 with HCl/$C_2H_5OH$(5N). The precipitated solid was filtered, and Compound VIII-8 was obtained by recrystallization in ethanol/water or methanol.

m.p=220.4-222.8° C. (dec). MS: m/z 481 (M$^+$).

$^1$HNMR (DMSO-d6): δ 0.66-0.69 (m, 3H, $CH_2CH_2CH_3$), 0.96-1.53 (m, 6H, $CH_2CH_2CH_2CH_3$), 2.17 (s, 3H, $CH_3$), 2.21 (s, 3H, $CH_3$), 2.80-2.96 (m, 9H, piperazine —CH), 3.99 (s, 3H, $OCH_3$), 4.59-4.61 (m, 1H, CH, J=8.4), 5.14 (d, 1H, OH), 6.83-8.05 (m, 8H, Ar—H).

EXAMPLE 9

VIII-9 (1SR,2RS)-N$^1$-benzyl-N$^4$-[1-butyl-2-(5'-chloro-6'-methoxyl-2'-naphthyl)hydroxyethyl]piperazine (erythro form)

4.20 g of N$^1$-benzyl-N$^4$-[1-butyl-2-carbonyl-2-(5-chloro-6-methoxynaphthalene-2-yl)]ethylpiperazine hydrochloride was synthesized using N$^1$-benzylpiperazine (10 mmol) and 2-(α-bromo-hexanone)-5-chloro-6-methoxynaphthaline (10 mmol), according to general method 2 to general method 4, in a yield of 78%, m.p=241.7-243.3° C. (dec). Then the reduction of carbonyl was performed upon N$^1$-benzyl-N$^4$-[1-butyl-2-carbonyl-2-(5-chloro-6-methoxynaphthalene-2-yl)]ethylpiperazine according to general method 5, and 3.73 g of N$^1$-benzyl-N$^4$-[1-butyl-2-hydroxy-2-(5-chloro-6-methoxynaphthalene-2-yl)]ethylpiperazine hydrochloride was obtained in a yield of 89%. The compound produced was transformed to free alkali thereof and separated by column chromatography. The erythro form was obtained and dissolved in ethanol, and adjusted to a pH of 2 with HCl/$C_2H_5OH$(5N). The precipitated solid was filtered, and Compound VIII-9 was obtained by recrystallization in ethanol/water or methanol. Element analysis of the compound showed that 2 molecules of crystal water were contained in the compound.

m.p=225.0-225.8° C. (dec). MS: m/z 467 (M$^+$).

$^1$HNMR (DMSO-d6): δ 0.72-1.60 (m, 9H, $CH_2CH_2CH_2CH_3$), 2.27-2.70 (m, 9H, CH+ piperazine —H), 3.40 (s, 2H, $CH_2$ Ph), 3.98 (s, 3H, $OCH_3$), 5.0 (d, 1H, CH, J=4.4), 5.10 (s, 1H, OH), 7.20-8.02 (m, 10H, Ar—H).

EXAMPLE 10

VIII-10 (1SR,2SR)-N$^1$-benzyl-N$^4$-[1-butyl-2-(5'-chloro-6'-methoxyl-2'-naphthyl)hydroxyethyl]piperazine (threo form)

4.20 g of N$^1$-benzyl-N$^4$-[1-butyl-2-carbonyl-2-(5-chloro-6-methoxynaphthalene-2-yl)]ethylpiperazine hydrochloride was synthesized using N$^1$-benzylpiperazine (10 mmol) and 2-(α-bromo-hexanone)-5-chloro-6-methoxyl naphthaline (10 mmol), according to general method 2 to general method 4, in a yield of 78%, m.p=241.7-243.3° C. (dec). Then the reduction of carbonyl was performed upon N$^1$-benzyl-N$^4$-[1-butyl-2-carbonyl-2-(5-chloro-6-methoxynaphthalene-2-yl)]ethylpiperazine according to general method 5, and 3.73 g of N$^1$-benzyl-N$^4$-[1-butyl-2-hydroxy-2-(5-chloro-6-methoxynaphthalene-2-yl)]ethylpiperazine hydrochloride was obtained in a yield of 89%. The compound produced was transformed to free alkali thereof and separated by column chromatography. The threo form was obtained and dissolved in ethanol, and adjusted to a pH of 2 with HCl/$C_2H_5OH$(5N). The precipitated solid was filtered, and Compound VIII-10 was obtained by recrystallization in ethanol/water or methanol. Element analysis showed that 2 molecules of crystal water were contained in the compound.

m.p=223.1-224.3° C. (dec). MS: m/z 467 (M$^+$).

$^1$HNMR (DMSO-d6): δ 0.66-1.50 (m, 9H, $CH_2CH_2CH_2CH_3$), 2.42-2.84 (m, 9H, CH+ piperazine —H), 3.49 (s, 2H, $CH_2$ Ph), 4.02 (s, 3H, $OCH_3$), 4.5 (d, 1H, CH, J=8.8), 5.10 (s, 1H, OH), 7.26-8.08 (m, 10H, Ar—H).

EXAMPLE 11

VIII-11 (1SR,2RS)-N$^1$-p-nitrobenzyl-N$^4$-[1-butyl-2-(5'-chloro-6'-methoxyl-2'-naphthyl)hydroxylethyl]piperazine (erythro form)

3.94 g of N$^1$-p-nitrobenzyl-N$^4$-[1-butyl-2-carbonyl-2-(5-chloro-6-methoxy naphthalene-2-yl)]ethylpiperazine hydrochloride was synthesized using N$^1$-p-nitrobenzylpiperazine (10 mmol) and 2-(α-bromo-hexanone)-5-chloro-6-methoxy-lnaphthaline (10 mmol), according to general method 2 to general method 4, in a yield of 77%, m.p=233.5-235.7° C. (dec).

Then the reduction of carbonyl was performed upon N$^1$-p-nitrobenzyl-N$^4$-[1-butyl-2-carbonyl-2-(5-chloro-6-methoxynaphthalene-2-yl)]ethylpiperazine according to general method 5, and 3.47 g of N$^1$-p-nitrobenzyl-N$^4$-[1-butyl-2-hydroxy-2-(5-chloro-6-methoxynaphthalene-2-yl)]ethylpiperazine hydrochloride was obtained in a yield of 88%. The compound produced was transformed to free alkali thereof and separated by column chromatography. The erythro form was obtained and dissolved in ethanol, and adjusted to a pH of 2 with HCl/$C_2H_5OH$(5N). The precipitated solid was filtered, and Compound VIII-11 was obtained by recrystallization in ethanol/water or methanol.

m.p=228.7-221.0° C. (dec). MS: m/z 512 (M$^+$).

$^1$HNMR (DMSO-d6): δ 0.72-1.60 (m, 9H, $CH_2CH_2CH_2CH_3$), 2.27-2.70 (m, 9H, CH+ piperazine —H), 3.40 (s, 2H, $CH_2$ Ph), 3.98 (s, 3H, $OCH_3$), 5.0 (d, 1H, CH, J=4.4), 5.10 (s, 1H, OH), 7.20-8.02 (m, 9H, Ar—H).

EXAMPLE 12

VIII-12 (1SR,2SR)-N$^1$-p-nitrobenzyl-N$^4$-[1-butyl-2-(5'-chloro-6'-methoxyl-2'-naphthyl)hydroxyethyl]piperazine (threo form)

3.94 g of N$^1$-p-nitrobenzyl-N$^4$-[1-butyl-2-carbonyl-2-(5-chloro-6-methoxy naphthalene-2-yl)]ethylpiperazine hydrochloride was synthesized using N$^1$-p-nitrobenzylpiperazine (10 mmol) and 2-(α-bromo-hexanone)-5-chloro-6-methoxyl naphthaline (10 mmol), according to general method 2 to general method 4, in a yield of 77%, m.p=233.5-235.7° C. (dec).

Then the reduction of carbonyl was performed upon N$^1$-p-nitrobenzyl-N$^4$-[1-butyl-2-carbonyl-2-(5-chloro-6-methoxynaphthalene-2-yl)]ethylpiperazine according to general method 5. 3.47 g of N$^1$-p-nitrobenzyl-N$^4$-[1-butyl-2-hydroxy-2-(5-chloro-6-methoxynaphthalene-2-yl)]ethylpiperazine hydrochloride was obtained in a yield of 88%. The compound produced was transformed to free alkali thereof and separated by column chromatography. The threo form was obtained and dissolved in ethanol, and adjusted to a pH of 2 with HCl/$C_2H_5OH$(5N). The precipitated solid was filtered, and Compound VIII-12 was obtained by recrystallization in ethanol/water or methanol.

m.p=226.8-229.0° C. (dec). MS: m/z 512 (M$^+$).

$^1$HNMR (DMSO-d6): δ 0.65-1.51 (m, 9H, CH$_2$CH$_2$CH$_2$CH$_3$), 2.49-2.97 (m, 9H, CH+ piperazine —H), 3.78 (s, 3H, OCH$_3$), 4.6 (d, 1H, CH, J=8.0), 5.14 (d, 1H, OH), 6.96-8.16 (m, 9H, Ar—H).

EXAMPLE 13

VIII-13 (1SR,2RS)-N$^1$-p-aminolbenzyl-N$^4$-[1-butyl-2-(5'-chloro-6'-methoxyl-2'-naphthyl)hydroxyethyl]piperazine (erythro form)

3.76 g of N$^1$-p-aminolbenzyl-N$^4$-[1-butyl-2-carbonyl-2-(5-chloro-6-methoxy naphthalene-2-yl)]ethylpiperazine hydrochloride was synthesized using N$^1$-p-aminobenzylpiperazine (10 mmol) and 2-(α-bromo-hexanone)-5-chloro-6-methoxylnaphthaline (10 mmol), according to general method 2 to general method 4, in a yield of 78%, m.p=233.6-235.9° C. (dec).

Then the reduction of carbonyl was performed upon N$^1$-p-aminobenzyl-N$^4$-[1-butyl-2-carbonyl-2-(5-chloro-6-methoxy naphthalene-2-yl)]ethylpiperazine according to general method 5, and 3.27 g of N$^1$-p-aminobenzyl-N$^4$-[1-butyl-2-hydroxy-2-(5-chloro-6-methoxynaphthalene-2-yl)]ethylpiperazine hydrochloride was obtained in a yield of 87%. The compound produced was transformed to free alkali thereof and separated by column chromatography. The erythro form was obtained and dissolved in ethanol, and adjusted to a pH of 2 with HCl/C$_2$H$_5$OH(5N). The precipitated solid was filtered, and Compound VIII-13 was obtained by recrystallization in ethanol/water or methanol.

m.p=219.4-221.0° C. (dec). MS: m/z 482 (M$^+$).

$^1$HNMR (DMSO-d6): δ 0.72-1.60 (m, 9H, CH$_2$CH$_2$CH$_2$CH$_3$), 2.27-2.70 (m, 9H, CH+ piperazine —H), 3.40 (s, 2H, CH$_2$ Ph), 3.98 (s, 3H, OCH$_3$), 4.0 (m, 2H, NH$_2$), 5.0 (d, 1H, CH, J=4.4), 5.10 (s, 1H, OH), 7.20-8.02 (m, 9H, Ar—H).

EXAMPLE 14

VIII-14 (1SR,2SR)-N$^1$-p-aminolbenzyl-N$^4$-[1-butyl-2-(5'-chloro-6'-methoxyl-2'-naphthyl)hydroxyethyl]piperazine (threo form)

3.76 g of N$^1$-p-aminobenzyl-N$^4$-[1-butyl-2-carbonyl-2-(5-chloro-6-methoxy naphthalene-2-yl)]ethylpiperazine hydrochloride was synthesized using N$^1$-p-aminobenzylpiperazine (10 mmol) and 2-(α-bromo-hexanone)-5-chloro-6-methoxylnaphthaline (10 mmol), according to general method 2 to general method 4, in a yield of 78%, m.p=233.6-235.9° C. (dec).

Then the reduction of carbonyl was performed upon N$^1$-p-aminobenzyl-N$^4$-[1-butyl-2-carbonyl-2-(5-chloro-6-methoxy naphthalene-2-yl)]ethylpiperazine according to general method 5, and 3.27 g of N$^1$-p-aminobenzyl-N$^4$-[1-butyl-2-hydroxy-2-(5-chloro-6-methoxynaphthalene-2-yl)]ethylpiperazine hydrochloride was obtained in a yield of 87%. The compound produced was transformed to free alkali thereof and separated by column chromatography. The threo form was obtained and dissolved in ethanol, and adjusted to a pH of 2 with HCl/C$_2$H$_5$OH(5N). The precipitated solid was filtered, and Compound VIII-14 was obtained by recrystallization in ethanol/water or methanol.

m.p=215.2-218.0° C. (dec). MS: m/z 482 (M$^+$).

$^1$HNMR (DMSO-d6): δ 0.65-1.51 (m, 9H, CH$_2$CH$_2$CH$_2$CH$_3$), 2.49-2.97 (m, 9H, CH+ piperazine —H), 3.78 (s, 3H, OCH$_3$), 3.87 (s, 3H, OCH$_3$), 4.0 (m, 2H, NH$_2$), 4.6 (d, 1H, CH, J=8.0), 5.14 (d, 1H, OH), 6.86-8.06 (m, 9H, Ar—H).

EXAMPLE 15

VIII-15 (1SR,2RS)-N$^1$-(3',4',5'-trimethoxybenzyl)-N$^4$-[1-butyl-2-(5'-chloro-6'-methoxyl-2'-naphthyl)hydroxyethyl]piperazine (erythro form)

4.18 g of N$^1$-(3',4',5'-trimethoxybenzyl)-N$^4$-[1-butyl-2-carbonyl-2-(5-chloro-6-methoxynaphthalene-2-yl)]ethylpiperazine hydrochloride was synthesized using N$^1$-(3',4',5'-trimethoxybenzyl)piperazine (10 mmol) and 2-(α-bromo-hexanone)-5-chloro-6-methoxylnaphthaline (10 mmol), according to general method 2 to general method 4, in a yield of 75%, m.p=235.5-238.6° C. (dec).

Then the reduction of carbonyl was performed upon N$^1$-(3',4',5'-trimethoxybenzyl)-N$^4$-[1-butyl-2-carbonyl-2-(5-chloro-6-methoxynaphthalene-2-yl)]ethylpiperazine according to general method 5, and 3.63 g of N$^1$-(3',4',5'-trimethoxybenzyl)-N$^4$-[1-butyl-2-hydroxy-2-(5-chloro-6-methoxynaphthalene-2-yl)]ethylpiperazine hydrochloride was obtained in a yield of 87%. The compound produced was transformed to free alkali thereof and separated by column chromatography. The erythro form was obtained and dissolved in ethanol, and adjusted to a pH of 2 with HCl/C$_2$H$_5$OH(5N). The precipitated solid was filtered, and Compound VIII-15 was obtained by recrystallization in ethanol/water or methanol.

m.p=221.3-223.6° C. (dec). MS: m/z 557 (M$^+$).

$^1$HNMR (DMSO-d6): δ 0.72-1.60 (m, 9H, CH$_2$CH$_2$CH$_2$CH$_3$), 2.27-2.70 (m, 9H, CH+ piperazine —H), 3.40 (s, 2H, CH$_2$ Ph), 3.70 (m, 9H, OCH$_3$), 3.98 (s, 3H, OCH$_3$), 4.0 (m, 2H, NH$_2$), 5.0 (d, 1H, CH, J=4.4), 5.10 (s, 1H, OH), 7.20-8.02 (m, 7H, Ar—H).

EXAMPLE 16

VIII-16 (1SR,2SR)-N$^1$-(3',4',5'-trimethoxybenzyl)-N$^4$-[1-butyl-2-(5'-chloro-6'-methoxyl-2'-naphthyl)hydroxyethyl]piperazine (threo form)

4.18 g of N$^1$-(3',4',5'-trimethoxybenzyl)-N$^4$-[1-butyl-2-carbonyl-2-(5-chloro-6-methoxynaphthalene-2-yl)]ethylpiperazine hydrochloride was synthesized using N1-(3',4',5'-trimethoxybenzyl)piperazine (10 mmol) and 2-(α-bromo-hexanone)-5-chloro-6-methoxylnaphthaline (10 mmol), according to general method 2 to general method 4, in a yield of 75%, m.p=235.5-238.6° C. (dec).

Then the reduction of carbonyl was performed upon N$^1$-(3',4',5'-trimethoxybenzyl)-N$^4$-[1-butyl-2-carbonyl-2-(5-chloro-6-methoxynaphthalene-2-yl)]ethylpiperazine according to general method 5, and 3.63 g of N$^1$-(3',4',5'-trimethoxybenzyl)-N$^4$-[1-butyl-2-hydroxy-2-(5-chloro-6-methoxynaphthalene-2-yl)]ethylpiperazine hydrochloride was obtained in a yield of 87%. The compound produced was transformed to free alkali thereof and separated by column chromatography. The threo form was obtained and dissolved in ethanol, and adjusted to a pH of 2 with HCl/C$_2$H$_5$OH(5N). The precipitated solid was filtered, and Compound VIII-16 was obtained by recrystallization in ethanol/water or methanol.

m.p=226.5-228.8° C. (dec). MS: m/z 557 (M$^+$).

$^1$HNMR (DMSO-d6): δ 0.65-1.51 (m, 9H, CH$_2$CH$_2$CH$_2$CH$_3$), 2.49-2.97 (m, 9H, CH+ piperazine —H), 3.70 (m, 9H, OCH$_3$), 3.78 (s, 3H, OCH$_3$), 3.87 (s, 3H, OCH$_3$), 4.6 (d, 1H, CH, J=8.0), 5.14 (d, 1H, OH), 6.86-8.06 (m, 7H, Ar—H).

EXAMPLE 17

VIII-17 (1SR,2RS)-N$^1$-α-phenemyl-N$^4$-[1-butyl-2-(5'-chloro-6'-methoxyl-2'-naphthyl)hydroxyethyl] piperazine (erythro form)

4.22 g of N$^1$-α-phenemyl-N$^4$-[1-butyl-2-carbonyl-2-(5-chloro-6-methoxynaphthalene-2-yl)]ethylpiperazine hydrochloride was synthesized using N$^1$-α-phenemyl piperazine (10 mmol) and 2-(α-bromo-hexanone)-5-chloro-6-methoxylnaphthaline (10 mmol), according to general method 2 to general method 4, in a yield of 78%, m.p=241.7-243.3° C. (dec).

Then the reduction of carbonyl was performed upon N$^1$-α-phenemyl-N$^4$-[1-butyl-2-carbonyl-2-(5-chloro-6-methoxynaphthalene-2-yl)]ethylpiperazine according to general method 5, and 3.75 g of N$^1$-α-phenemyl-N$^4$-[1-butyl-2-hydroxy-2-(5-chloro-6-methoxynaphthalene-2-yl)]ethylpiperazine hydrochloride was obtained in a yield of 89%. The compound produced was transformed to free alkali thereof and separated by column chromatography. The erythro form was obtained and dissolved in ethanol, and adjusted to a pH of 2 with HCl/C$_2$H$_5$OH(5N). The precipitated solid was filtered, and Compound VIII-17 was obtained by recrystallization in ethanol/water or methanol.

m.p=235.0-237.6° C. (dec). MS: m/z 481.1 (M$^+$).

$^1$HNMR (DMSO-d6): δ 0.54-0.63 (m, 3H, CH$_2$CH$_2$CH$_3$), 0.78-1.24 (m, 6H, CH$_2$CH$_2$CH$_3$), 1.57-1.75 (m, 3H, CH CH$_3$), 1.83-1.86 (m, 2H, CH$_2$CH$_2$CH$_2$CH$_3$), 3.44-3.59 (m, 8H, piperazine —H), 3.99 (s, 3H, OCH$_3$), 4.57 (m, 1H, CH$_3$-CH-Ph), 4.57 (m, 1H, CH), 5.66-5.67 (d, 1H, CH, J=4.8), 7.48-8.11 (m, 10H, Ar—H).

EXAMPLE 18

VIII-18 (1SR,2SR)-N$^1$-α-phenemyl-N$^4$-[1-butyl-2-(5'-chloro-6'-methoxyl-2'-naphthyl)hydroxyethyl] piperazine (threo form)

4.22 g of N$^1$-α-phenemyl-N$^4$-[1-butyl-2-carbonyl-2-(5-chloro-6-methoxynaphthalene-2-yl)]ethylpiperazine hydrochloride was synthesized using N$^1$-α-phenemylpiperazine (10 mmol) and 2-(α-bromo-hexanone)-5-chloro-6-methoxylnaphthaline (10 mmol), according to general method 2 to general method 4, in a yield of 78%, m.p=241.7-243.3° C. (dec).

Then the reduction of carbonyl was performed upon N$^1$-α-phenemyl-N$^4$-[1-butyl-2-carbonyl-2-(5-chloro-6-methoxynaphthalene-2-yl)]ethylpiperazine according to general method 5, and 3.75 g of N$^1$-α-phenemyl-N$^4$-[1-butyl-2-hydroxy-2-(5-chloro-6-methoxynaphthalene-2-yl)]ethylpiperazine hydrochloride was obtained in a yield of 89%. The compound produced was transformed to free alkali thereof and separated by column chromatography. The threo form was obtained and dissolved in ethanol, and adjusted to a pH of 2 with HCl/C$_2$H$_5$OH(5N) The precipitated solid was filtered, and Compound VIII-18 was obtained by recrystallization in ethanol/water or methanol. m.p=224.0-226.1° C. MS: m/z 481 (M$^+$).

$^1$HNMR (DMSO-d6): δ 0.61-0.65 (m, 3H, CH$_2$CH$_2$CH$_3$), 0.88-1.06 (m, 6H, CH$_2$CH$_2$CH$_3$), 1.28-1.29 (m, 3H, CH CH$_3$), 2.33-2.76 (m, 8H, piperazine), 2.50-2.510 (m, 1H, CH—N), 3.25-3.39 (m, 1H, CH$_3$—CH-Ph), 3.99 (s, 3H, OCH$_3$), 4.47-4.51 (m, 1H, CH, J=8.4), 5.05 (d, 1H, OH), 7.23-8.03 (m, 10H, Ar—H).

EXAMPLE 19

VIII-19 (1SR,2RS)-N$^1$-benzhydryl-N$^4$-[1-butyl-2-(5'-chloro-6'-methoxyl-2'-naphthyl)hydroxyethyl] piperazine (erythro form)

4.68 g of N$^1$-benzhydryl-N$^4$-[1-butyl-2-carbonyl-2-(5-chloro-6-methoxy naphthalene-2-yl)]ethylpiperazine hydrochloride was synthesized using N$^1$-benzhydryl piperazine (10 mmol) and 2-(α-bromo-hexanone)-5-chloro-6-methoxyl naphthaline (10 mmol), according to general method 2 to general method 4, in a yield of 76%, m.p=212.9-215.2° C. (dec).

Then the reduction of carbonyl was performed upon N$^1$-benzhydryl-N$^4$-[1-butyl-2-carbonyl-2-(5-chloro-6-methoxynaphthalene-2-yl)]ethyl piperazine according to general method 5, and 4.83 g of N$^1$-benzhydryl-N$^4$-[1-butyl-2-hydroxy-2-(5-chloro-6-methoxynaphthalene-2-yl)]ethylpiperazine hydrochloride was obtained in a yield of 85%. The compound produced was transformed to free alkali thereof and separated by column chromatography. The erythro form was obtained and dissolved in ethanol, and adjusted to a pH of 2 with HCl/C$_2$H$_5$OH(5N). The precipitated solid was filtered, and Compound VIII-19 was obtained by recrystallization in ethanol/water or methanol. m.p=183.0-184.6° C. (dec). MS: m/z 543 (M$^+$).

$^1$HNMR (DMSO-d6): δ 0.71-1.60 (m, 9H, CH$_2$CH$_2$CH$_2$CH$_3$), 2.24-2.74 (m, 9H, CH+ piperazine —H), 4.22 (s, 1H, CH Ph$_2$), 3.98 (s, 3H, OCH$_3$), 5.0 (d, 1H, CH, J=3.6), 5.11 (d, 1H, OH), 7.14-8.01 (m, 15H, Ar—H).

EXAMPLE 20

VIII-20 (1SR,2SR)-N$^1$-benzhydryl-N$^4$-[1-butyl-2-(5'-chloro-6'-methoxyl-2'-naphthyl)hydroxyethyl] piperazine (threo form)

4.68 g of N$^1$-benzhydryl-N$^4$-[1-butyl-2-carbonyl-2-(5-chloro-6-methoxy naphthalene-2-yl)]ethylpiperazine hydrochloride was synthesized using N$^1$-benzhydryl piperazine (10 mmol) and 2-(α-bromo-hexanone)-5-chloro-6-methoxyl naphthaline (10 mmol), according to general method 2 to general method 4, in a yield of 76%, m.p=212.9-215.2° C. (dec).

Then the reduction of carbonyl was performed upon N$^1$-benzhydryl-N$^4$-[1-butyl-2-carbonyl-2-(5-chloro-6-methoxynaphthalene-2-yl)]ethylpiperazine according to general method 5, and 4.13 g of N$^1$-benzhydryl-N$^4$-[1-butyl-2-hydroxy-2-(5-chloro-6-methoxynaphthalene-2-yl)]ethylpiperazine hydrochloride was obtained in a yield of 85%. The compound produced was transformed to free alkali thereof and separated by column chromatography. the threo form was obtained and dissolved in ethanol, and adjusted to a pH of 2 with HCl/C$_2$H$_5$OH(5N). The precipitated solid was filtered, and Compound VIII-20 was obtained by recrystallization in ethanol/water or methanol. m.p=179.3-181.1° C. (dec).

MS: m/z 543 (M$^+$).

$^1$HNMR (DMSO-d6): δ 0.63-1.46 (m, 9H, CH$_2$CH$_2$CH$_2$CH$_3$), 2.33-2.82 (m, 9H, CH+ piperazine —H), 4.28 (s, 1H, CH Ph$_2$), 3.98 (s, 3H, OCH$_3$), 4.5 (d, 1H, CH, J=8.4), 5.06 (s, 1H, OH), 7.16-8.03 (m, 15H, Ar—H).

EXAMPLE 21

VIII-21 (1SR,2RS)-N$^1$-cinnamyl-N$^4$-[1-butyl-2-(5'-chloro-6'-methoxyl-2'-naphthyl)hydroxyethyl]piperazine (erythro form)

4.61 g of N$^1$-cinnamyl-N$^4$-[1-butyl-2-carbonyl-2-(5-chloro-6-methoxy naphthalene-2-yl)]ethylpiperazine hydrochloride was synthesized using N$^1$-cinnamylpiperazine (10 mmol) and 2-(α-bromo-hexanone)-5-chloro-6-methoxyl-naphthaline (10 mmol), according to general method 2 to general method 4, in a yield of 82%, m.p=232.2-234.0° C. (dec).

Then the reduction of carbonyl was performed upon N$^1$-cinnamyl-N$^4$-[1-butyl-2-carbonyl-2-(5-chloro-6-methoxynaphthalene-2-yl)]ethylpiperazine according to general method 5, and 4.19 g of N$^1$-cinnamyl-N$^4$-[1-butyl-2-hydroxy-2-(5-chloro-6-methoxynaphthalene-2-yl)]ethylpiperazine hydrochloride was obtained in a yield of 91%. The compound produced was transformed to free alkali thereof and separated by column chromatography. The erythro form was obtained and dissolved in ethanol, and adjusted to a pH of 2 with HCl/C$_2$H$_5$OH(5N). The precipitated solid was filtered, and Compound VIII-21 was obtained by recrystallization in ethanol/water or methanol. m.p=228.8-230.1° C. (dec). MS: m/z 493 (M$^+$).

$^1$HNMR (DMSO-d6): 0.73-1.60 (m, 9H, CH2CH2CH2CH3), 2.31-3.04 (m, 11H, CH+ CH2+ piperazine —H), 3.98 (s, 3H, OCH3), 4.9 (d, 1H, CH, J=4.0), 5.11 (d, 1H, OH), 6.23-6.52 (m, 2H, CH=CH), 7.22-8.02 (m, 10H, Ar—H).

EXAMPLE 22

VIII-22 (1SR,2SR)-N$^1$-cinnamyl-N$^4$-[1-butyl-2-(5'-chloro-6'-methoxyl-2'-naphthyl)hydroxyethyl]piperazine (threo form)

4.61 g of N$^1$-cinnamyl-N$^4$-[1-butyl-2-carbonyl-2-(5-chloro-6-methoxynaphthalene-2-yl)]ethylpiperazine hydrochloride was synthesized using N$^1$-cinnamyl piperazine (10 mmol) and 2-(α-bromo-hexanone)-5-chloro-6-methoxyl-naphthaline (10 mmol), according to general method 2 to general method 4, in a yield of 82%, m.p=232.2-234.0° C. (dec).

Then the reduction of carbonyl was performed upon N$^1$-cinnamyl-N$^4$-[1-butyl-2-carbonyl-2-(5-chloro-6-methoxynaphthalene-2-yl)]ethyl piperazine according to general method 5, and 4.19 g of N$^1$-cinnamyl-N$^4$-[1-butyl-2-hydroxy-2-(5-chloro-6-methoxynaphthalene-2-yl]ethylpiperazine hydrochloride was obtained in a yield of 91%. The compound produced was transformed to free alkali thereof and separated by column chromatography. The threo form was obtained and dissolved in ethanol, and adjusted to a pH of 2 with HCl/C$_2$H$_5$OH(5N). The precipitated solid was filtered, and Compound VIII-22 was obtained by recrystallization in ethanol/water or methanol. m.p=194.1-195.6° C. (dec).

MS: m/z 493 (M$^+$).
$^1$HNMR (DMSO-d6): δ 0.36-1.49 (m, 9H, CH$_2$CH$_2$CH$_2$CH$_3$), 2.43-3.27 (m, 11H, CH+ CH$_2$+ piperazine —H), 3.98 (s, 3H, OCH$_3$), 4.5 (d, 1H, CH, J=8.0), 5.18 (s, 1H, OH), 6.24-6.55 (m, 2H, CH=CH), 7.21-8.05 (m, 10H, Ar—H).

EXAMPLE 23

Synthesis of (S)-2-(1,3-dicarbonylisoindole)hexanoic acid (2)

6.55 g of L-norleucine (0.05 mol), 7.40 g of phthalic anhydride (0.05 mol), 0.8 ml of triethylamine were added into 150 ml of toluene under stirring at 110° C. After reaction by refluxing for 24 hours, the reaction was complete. The solvent was evaporated after standing to cool down, and 50 ml of water was added. Extraction was performed with ethyl acetate (50 ml×3), and the ethyl acetate layer was washed with saturated NaCl solution, dried by anhydrous MgSO$_4$. The solvent of the filtrate was evaporated after filtrating the mixture, and 12.28 g of white solid was obtained in a yield of 90.3%.

MS: m/z 262 (M+). $^1$HNMR (DMSO-d6): δ 0.86-1.37 (m, 9H, CH$_2$CH$_2$CH$_2$CH$_3$), 4.46 (m, 1H, CH), 7.25-7.86 (m, 4H, Ar—H).

EXAMPLE 24

Preparation of (R)-2-(1,3-dicarbonylisoindole)hexanoic acid was same as that of (S)-2-(1,3-dicarbonylisoindole)hexanoic acid (2). The yield was 87.6%.

MS: m/z 262 (M+). $^1$HNMR (DMSO-d6): δ 0.90-1.25 (m, 9H, CH$_2$CH$_2$CH$_2$CH$_3$), 4.68 (m, 1H, CH), 7.42-7.91 (m, 4H, Ar—H).

EXAMPLE 25

Synthesis of (S)-2-[2-(1,3-dicarbonylisoindole)hexanoyl]-5-chloo-6-methoxyl naphthaline (5)

10.45 g of Compound 2 (0.04 mol) was dissolved in 100 ml of dichloromethane at 0° C., and 8.15 ml (0.1 mol) of oxalyl chloride was added dropwise in ice-bath. After dropping, 8 drops of pyridine was added. The temperature increased slowly to room temperature and the mixture was stirred for 20 hours. Superfluous acyl chloride and solvent was evaporated by rotary evaporation at 35° C., the concentrate was dissolved in 100 ml of dichloromethane. 9.25 g of Compound 4 (0.048 mol) and 6.41 g of anhydrous AlCl$_3$ (0.048 mol) were added to react for 30 hours at room temperature. The reactant was pooled slowly into the mixture of 1N HCl (100 ml)/ice/dichloromethane (100 ml), stirred and stood to allow layers separated. The aqueous layer was extracted with dichloromethane (100 ml×2). The dichloromethane layers were pooled, then washed with saturated NaCl solution, dried by anhydrous MgSO$_4$. The solvent of the filtrate was evaporated after filtration. Dark brown oily substance was obtained, and separated by column chromatography (neutral alumina, petroleum ether:ethyl acetate=3:1). 4.68 g of light yellow oily substance was obtained in a yield of 26.8%. MS: m/z 438 (M+). $^1$HNMR (DMSO-d6): δ 0.96-1.77 (m, 9H, CH$_2$CH$_2$CH$_2$CH$_3$), 3.73 (s, 3H, OCH$_3$), 5.09 (m, 1H, CH), 7.64-8.34 (m, 9H, Ar—H).

EXAMPLE 26

Preparation of (R)-2-[2-(1,3-dicarbonylisoindole)hexanoyl]-5-chloro-6-methoxyl naphthaline was same as that of (S)-2-[2-(1,3-dicarbonylisoindole)hexanoyl]-5-chloro-6-methoxylnaphthaline (5) in a yield of 28.4%. MS: m/z 438 (M+).

$^1$HNMR (DMSO-d6): δ 1.03-1.62 (m, 9H, CH$_2$CH$_2$CH$_2$CH$_3$), 3.10 (s, 3, OCH$_3$), 5.14 (m, 1H, CH), 7.35-8.11 (m, 9H, Ar—H).

EXAMPLE 27

Synthesis of (2S)-2-[1-hydroxy-2-(1,3-dicarbonyl-isoindole)hexyl]-5-chloro-6-methoxyl naphthaline (6)

4.36 g of Compound 5 (0.01 mol) was dissolved in the mixture of 19.2 ml of toluene and 12.6 ml of isopropanol, then 10.2 g (0.05 mol) of aluminium isopropoxide was added to react at 100° C. for 4 hours. After the reaction was complete, the mixture was cooled down, the solvent was evaporated, and 1N of HCl (50 ml) was added. Extraction was performed with ethyl acetate (50 ml×3). The ethyl acetate layer was washed with a small amount of water and saturated NaCl solution, dried by anhydrous $MgSO_4$. The solvent was evaporated after filtration, and 4.32 g of light yellow solid was obtained in a yield of 98.6%. MS: m/z 439 (M+). $^1$HNMR (DMSO-d6): δ 0.96-1.58 (m, 9H, $CH_2CH_2CH_2CH_3$), 3.73 (s, 3, $OCH_3$), 4.05 (m, 1H, CHN), 5.12 (m, 1H, CHOH), 7.34-8.08 (m, 9H, Ar—H).

EXAMPLE 28

Preparation of (2R)-2-[1-hydroxy-2-(1,3-dicarbonylisoindole)hexyl]-5-chloro-6-methoxylnaphthaline was same as that of (2S)-2-[1-hydroxy-2-(1,3-dicarbonyl isoindole)hexyl]-5-chloro-6-methoxylnaphthaline (6) in a yield of 97.4%. MS: m/z 439 (M+). $^1$HNMR (DMSO-d6): δ 0.89-1.44 (m, 9H, $CH_2CH_2CH_2CH_3$), 3.70 (s, 3, $OCH_3$), 4.19 (m, 1H, CHN), 5.07 (m, 1H, CHOH), 7.12-8.00 (m, 9H, Ar—H).

EXAMPLE 29

Synthesis of (1S)-2-(5-chloro-6-methoxylnaphthaline)-2-hydroxy-1-butyl ethylamine (7)

2.15 g of Compound 6 (0.005 mol) was dissolved in 15 ml of methanol, 5 ml of hydrazine hydrate (0.01 mol) was added. The mixture was stirred for 3 hours at room temperature and white solid was produced. After filtration, the solvent of filtrate was evaporated, and extraction was performed with water (20 ml)/dichloromethane (20 ml×3). The pooled dichloromethane layer was washed with saturated NaCl solution, dried with anhydrous $MgSO_4$. After filtration, the solvent of filtrate was evaporated, and 1.13 g of white solid was obtained in a yield of 73.4%. MS: m/z 309 ($M^+$). $^1$HNMR (DMSO-d6): δ 0.93-1.54 (m, 9H, $CH_2CH_2CH_2CH_3$), 3.08 (m, 1H, CHN), 3.77 (s, 3, $OCH_3$), 4.75 (m, 1H, CHOH), 7.50-8.17 (m, 5H, Ar—H).

EXAMPLE 30

Preparation of (1R)-2-(5-chloro-6-methoxylnaphthaline)-2-hydroxy-1-butylethyl amine was same as that of (1S)-2-(5-chloro-6-methoxylnaphthaline)-2-hydroxy-1-butylethylamine (7) in a yield of 70.1%. MS: m/z 309 ($M^+$). $^1$HNMR (DMSO-d6): δ 1.11-1.77 (m, 9H, $CH_2CH_2CH_2CH_3$), 3.14 (m, 1H, CHN), 3.58 (s, 3, $OCH_3$), 4.69 (m, 1H, CHOH), 7.75-8.29 (m, 5H, Ar—H).

EXAMPLE 31

Preparation of (1S,2R)-$N^1$-benzyl-$N^4$-[1-butyl-2-hydroxy-2-(5'-chloro-6'-methoxyl-2')-naphthylethyl]piperazine hydrochloride (IX-23) and (1S,2S)-$N^1$-benzyl-$N^4$-[1-butyl-2-hydroxy-2-(5'-chloro-6'-methoxyl-2')-naphthylethyl]piperazine hydrochloride (IX-24).

To 0.924 g of compound 7 (0.003 mol) were added 10 ml of acetonitrile, 2 ml of triethylamine and 1.624 g of compound 8 (0.007 mol, prepared c.f. U.S. Pat. No. 4,748,726), the mixture was heated and refluxed for 20 hours till the reaction was complete detected by TLC. Acetonitrile was evaporated, extraction was performed with chloroform (50 ml×3) and water. The chloroform layers was pooled and dried by $MgSO_4$. Chloroform was evaporated, and yellow oily substance was obtained, which was the mixture of two isomers (9). MS: m/z 465 (M+).

The mixture (9) was separated by silica gel column chromatography with dichloromethane:methanol=200:1 as the eluant. 0.47 g of yellow oily (1S,2S) isomer (yield: 34%) was firstly eluted and dissolved in 20 ml of methanol. Hydrochloric acid/ethanol was used to adjust the pH to 2. White solid precipitated, and 0.25 g of white product was obtained by filtration.

0.12 g of yellow oily (1S,2R) isomer (yield: 8.5%) was eluted later and dissolved in 10 ml of methanol. Hydrochloric acid/ethanol was used to adjust the pH to 2. Light yellow solid precipitated, and 0.05 g of yellow product was obtained by filtration and heating to dryness.

IX-23: mp: 225.0~225.8° C. (dec); MS: m/z 467 (M+); $^1$HNMR (DMSO-d6): δ 0.36-1.86 (m, 9H, $CH_2CH_2CH_2CH_3$), 3.54-3.80 (m, 9H, CH+piperazine-H), 3.96 (s, 2H, $CH_2$-Ph), 4.42 (s, 3H, $OCH_3$), 5.519-5.524 (d, 1H, CH, J=2.0), 7.43-8.14 (m, 10H, Ar—H).

IX-24: mp: 223.1~224.3° C. (dec); MS: m/z 467 (M+); $^1$HNMR (DMSO-d6): δ 0.33-1.58 (m, 9H, $CH_2CH_2CH_2CH_3$), 3.62-3.79 (m, 9H, CH+ piperazine-H), 3.95 (s, 2H, $CH_2$-Ph), 4.42 (s, 3H, $OCH_3$), 4.913-4.937 (d, 1H, CH, J=9.6), 7.43-8.17 (m, 10H, Ar—H).

EXAMPLE 32

Preparation of (1S,2S)-$N^1$-benzyl-$N^4$-[1-butyl-2-hydroxy-2-(5'-chloro-6'-methoxyl-2')-naphthylethyl]piperazine hydrochloride (IX-25) and (1S,2R)-$N^1$-benzyl-$N^4$-[1-butyl-2-hydroxy-2-(5'-chloro-6'-methoxyl-2')-naphthylethyl]piperazine hydrochloride (IX-26) were same as Example 31.

IX-25: mp: 225.0~225.8° C. (dec); MS: m/z 467 (M+); $^1$HNMR (DMSO-d6): δ 0.36-1.86 (m, 9H, $CH_2CH_2CH_2CH_3$), 3.54-3.80 (m, 9H, CH+ piperazine-H), 3.96 (s, 2H, $CH_2$-Ph), 4.42 (s, 3H, $OCH_3$), 5.519-5.524 (d, 1H, CH, J=2.0), 7.43-8.14 (m, 10H, Ar—H).

IX-26: mp: 223.1~224.3° C. (dec); MS: m/z 467 (M+); $^1$HNMR (DMSO-d6): δ 0.33-1.58 (m, 9H, $CH_2CH_2CH_2CH_3$), 3.62-3.79 (m, 9H, CH+ piperazine-H), 3.95 (s, 2H, $CH_2$-Ph), 4.42 (s, 3H, $OCH_3$), 4.913-4.937 (d, 1H, CH, J=9.6), 7.43-8.17 (m, 10H, Ar—H).

EXAMPLE 33

| Tablet: | |
| --- | --- |
| derivative of the present invention | 10 mg |
| sucrose | 150 mg |
| corn starch | 38 mg |
| calcium stearate | 2 mg |

Preparation: the active ingredient was mixed with sucrose and corn starch, then the mixture was wetted by adding water, stirred evenly, dried, crushed and screened, then calcium stearate was added. The mixture obtained was stirred evenly and then pressed into tablets. The tablet weight was 200 mg per tablet, containing 10 mg of active ingredient.

EXAMPLE 34

| Injection: | |
|---|---|
| Derivative of the present invention | 20 mg |
| water for injection | 80 mg |

Preparation: the active ingredient was dissolved and mixed evenly with water for injection, then filtered. The mixture obtained was distributed into ampoules under sterile conditions. The weight was 10 mg ampoule per ampoule, containing 2 mg of active ingredient.

EXAMPLE 35

Inhibition Effect of the Compounds on the Reuptake of 5-HT, NA and DA by Brain Synaptosomes Studies on the reuptake of monoamine neurotransmitters by brain synaptosomes was performed, which is a currently important mean adopted in the worldwide in pharmacological studies of central nervous. This method can not only be used to study the action mechanism of a drug, but also be used for screening new drugs acting by this mechanism. In the present invention, studies on the inhibition effect of the compounds on the reuptake of 5-HT, NA and DA by brain synaptosomes was performed, using venlafaxine (an effective dual inhibitor on the reuptake of 5-HT and NA) and 6-hydroxy DA as the positive controls.

1. Preparation of Rat Brain Synaptosomes

Male SD rats were sacrificed by cervical dislocation and then the brains thereof were taken out rapidly by decollation and placed on ice. Related rain tissues (for [$^3$H]5-HT and [$^3$H]NA reuptake experiment, prefrontal cortex was taken; for [$^3$H]DA reuptake experiment, striatum was taken) were separated and weighed. 10 times (V/W) of 0.32 mol/L ice-cold sucrose solution was added and was homogenized electrically with glass-teflon. The homogenate was centrifugated at 4° C. at 1000 g×10 min. Then the supernatant was taken and centrifugated at 4° C. at 17000 g×20 min. The precipitation was suspended in 30 volume of KRH Buffer (125 mM NaCl, 4.8 mM KCl, 1.2 mM CaCl$_2$, 1.2 mM MgSO$_4$, 1.0 mM KH$_2$PO$_4$, 22 mM NaHCO$_3$, 25 mM HEPES, 10 mM Glucose, 10 µM Pargyline, 0.2 mg/ml Ascorbic Acid) and then was preserved in an ice bath for use. (for NA reuptake experiment, the cortex needed was suspended in 20 volume of KRH Buffer)

2. [$^3$H]5-HT/NA/DA Reuptake Experiments

Stock solution of the test substance was thawed immediately before use and diluted with KBH Buffer to 100 µmol/L, 50 µl thereof was added in 500 µl of total reaction system, and the final concentration was 10 µmol/L. Then 50 µl suspended synaptic prepared above was added and mixed evenly, incubated in water bath for 30 min at 37° C. Then 10 mmol/L [$^3$H] 5-HT (50 nmol/L [$^3$H]DA or 60 nmol/L [$^3$H]NA) was added. After incubated at 37° C. for 10 min, the reaction system was immediately taken out and the reaction was stopped by adding 2 ml of ice-cold 150 mmol/L Tris-HCl buffer solution. The samples were collected on the circular fiberglass membrane by vacuum filtration, and the membrane was washed 3 times with 3 ml of ice-cold Tris-HCl buffer solution. The filtration membrane was removed, baked for 15 min in a far-infrared oven and placed into an EP tube. 1.5 ml scintillation fluid was added overnight and was tested by liquid scintillation counter. For the solvent control total binding tube and the non-specific binding tube, no test substance was added; for the total binding tube, 50 µl solvent was added.

3. Results:

Taking the inhibitory rate of 0.1 mM of venlafaxine and 6-hydroxy DA on reuptake of monoamine as 100%, the inhibitory intensity of the compounds, compared with venlafaxine and 6-hydroxy DA was shown in Table 3.

TABLE 3 inhibitory percent (%) on reuptake of 5-HT, NA and DA by brain synaptosomes

| compounds | Inhibition on the reuptake of 5-HT(%) | inhibition on the reuptake of NA(%) | inhibition on the reuptake of DA(%) |
|---|---|---|---|
| venlafaxine | 100 | 100 | / |
| 6-hydroxy DA | / | / | 100 |
| VIII-3 | 65.1 | 144 | 96 |
| VIII-4 | 23 | 146.5 | 68 |
| VIII-9 | 125 | 155.2 | 117 |
| VIII-10 | 136 | 145 | 133 |
| VIII-19 | 73.4 | 103.6 | 95 |
| VIII-20 | 0 | 78 | 57 |
| VIII-21 | 81 | 87.5 | 90 |
| VIII-22 | 82.3 | 78.9 | 94 |

4. Conclusion

The 1-butyl-2-hydroxy aralkyl piperazine derivatives of the present invention, were triple reuptake inhibitors, which have strong in vitro inhibition on the reuptake of monoamine transmitters DA, NE and 5-HT. The triple reuptake-inhibition activity of preferred compounds VIII-9 and VIII-10 were stronger than that of the positive control venlafaxine.

EXAMPLE 36

Determination of IC$_{50}$ of Preferred Compounds VIII-9 and VIII-10 for Inhibiting Reuptake of 5-HT, NA and DA by Brain Synaptosomes 1. Preparation of Rat Brain Synaptosomes (the Same as Example 35)

2. Research on Reuptake Inhibition (IC$_{50}$) on [$^3$H]5-HT/NA/DA

The compounds were used for the studies on inhibition effect (IC$_{50}$) on reuptake of [$^3$H]5-HT/NA/DA. At least 5 concentrations each time were settled for each test compound. Each concentration was determined by the average of double twin tubes and the test was repeated for more than 3 times. A series of concentrations of the compounds were prepared by gradient dilution before use. 50 µl thereof was added in total reaction system. Then 50 µl suspended synaptic membrane was added and mixed evenly, incubated in water bath at 37° C. for 30 min. Then 10 nmol/L [$^3$H] 5-HT (or 50 nmol/L [$^3$H]DA or 40 nmol/L [$^3$H]NA) was added and incubated in water bath at 37° C. for 10 min (for [$^3$H]NA, incubated for 5 min). For the [$^3$H]5-HT reuptake experiment, 50 µL of fluoxetine (100 µmol/L) was added to the non-specific binding tube; for the [$^3$H]DA reuptake experiment, 50 µL of cocaine (600 µmol/L) was added to the non-specific binding tube; for the [$^3$H]NA reuptake experiment, 50 µL of desipramine (100 µmol/L) was added to the non-specific binding tube; for the solvent control, solvent was added to the total binding tube, but no test compound added.

3. Date Processing specific binding CPM value for each test sample tube=total binding CPM value for each test sample tube−non-specific binding CPM value for each test sample tube; inhibition rate of the compound (%) on the reuptake of [$^3$H]5-HT/NA/DA by prefrontal cortex and striatum=100%−specific binding for each test sample tube (CPM value)/solvent specific binding (CPM value)×100%. Sigmoidal curve fitting was performed for the data obtained from all of the test drugs by Origin 6.1, and the $IC_{50}$ value was calculated.

4. $IC_{50}$ Determination Results

Inhibition of the compounds ($IC_{50}$) on the reuptake of 5-HT, NA and DA by prefrontal cortex and striatum was shown in Table 4.

TABLE 4 inhibition effect of the compounds on the reuptake of [$^3$H]5-HT/NA/DA $IC_{50}$(mean ± SE, n = 3~4)

| compounds | $IC_{50}$ (nmol/L) | | |
|---|---|---|---|
| | [$^3$H]5-HT | [$^3$H]NA | [$^3$H]DA |
| venlafaxine | 145 | 1420 | 3070 |
| SIPIyy24 | 200 | 1000 | No activity detected |
| SIPI5286 | 12 | 185 | 1150 |
| VIII-9 | 73.28 | 2.8 | 2.1 |
| VIII-10 | 271.51 | 4726.1 | 165.4 | note:
Compound SIPIyy24 was the preferred compound in Patent ZL02111934.1;
Compound SIPI5286 was the preferred compound in Patent ZL200510030354.1.

5. Conclusion

Compound VIII-10 had a comparable in vitro inhibition activity on the reuptake of 5-HT and NA, compared with venlafaxine and SIPIyy24, and had a stronger inhibition activity on the reuptake of DA, compared with venlafaxine, SIPIyy24 and SIPI5286; Compound VIII-9 had a stronger inhibition activity on the reuptake of the three kinds of monoamine transmitters, compared with venlafaxine, SIyy24 and SIPI5286.

EXAMPLE 37

In Vitro Inhibition Effect of the Four Optical Isomers IX-23~IX-26 on the Reuptake Of the Three Monoamine Transmitters 1. Experiment Materials and Methods

| experiments | materials | control | Methods (references) |
|---|---|---|---|
| NE reuptake | Rat hypothalamus synaptosome | protriptyline | Perovic and Muller W. E. G. Pharnacological profile of hypericum extract on serotonin uptake by postsynaptic receptors. Arzneim-Forsch. Drug Res., 1995, 45: 1145-1148. |
| DA reuptake | Rat striatum synaptosome | GBR 12909 | Janowsky; Berger, P.; Vocci, F.; Labarca, R., Skolnick, P.; Paul, S. M. Characterization of sodium-dependent[3H]GBR-12935 binding in brain: a radioligand for selective labelling of the dopamine transport complex. J. Neurochem., 1986, 46: 1272-1276. |
| 5-HT reuptake | Rat brain synaptosome | imipramine | Perovic and Muller W. E. G. Pharmacological profile of hypericum extract on serotonin uptake by postsynaptic receptors. Arzneim-Forsch. Drug Res., 1995, 45: 1145-1148. |

2. Experiment Conditions

| experiments | label | incubation | reaction product | detection method |
|---|---|---|---|---|
| NE reuptake | [3H]NE (μ0.2 Ci/ml) | 20 min./37° C. | [3H]NE binding synaptosome | scinticounting |
| DA reuptake | [3H] DA (μ0.2 Ci/ml) | 15 min./37° C. | [3H] DA binding synaptosome | scinticounting |
| 5-HT reuptake | [3H] 5-HT (μ0.2 Ci/ml) | 15 min./37° C. | [3H] 5-HT binding synaptosome | scinticounting |

3. Experiment Results ($IC_{50}$ Value was Obtained by Nonlinear Regression Analysis of Inhibition Rate/Concentration Response Curve)

| Compounds | configuration | $IC_{50}$ (nM) | | |
|---|---|---|---|---|
| | | 5-HT | NE | DA |
| IX-23 | (1S, 2R) | 1900 | 2100 | 1000 |
| IX-24 | (1S, 2S) | 3100 | 1400 | 1100 |
| IX-25 | (1R, 2S) | 830 | 140 | 670 |
| IX-26 | (1R, 2R) | 1200 | 1200 | 1100 |

4. Conclusion

The four optical isomers IX-23~IX-26 had strong in vitro inhibition activity on the reuptake of the three monoamine transmitters DA, NE and 5-HT, and belonged to triple reuptake inhibitors.

EXAMPLE 38

Studies on the In Vivo Antidepression Activity in Animals of Preferred Compounds VIII-9 and VIII-10

Studies was carried out on the in vivo antidepression effect of compounds VIII-9 and VII-10 using the mice Forced Swimming Test in Learned Helplessness Experiment (Zhang Juntian, Modern Pharmacological Experiments Mothods (first volume). Beijing Medical University and Peking Union Medical University Joint Publishing House, 1998: 1064-1066), with venlafaxine as the positive control.

TABLE 5 effect of single oral administration on swimming test for ICR mice (n = 12, x̄±SD)

| groups | dosage | swimming test: immobility time(s) |
|---|---|---|
| blank control | N.S | 109.4 ± 66.19 |
| venlafaxine | 50 mg/kg | 46.5 ± 25.14** |

TABLE 5-continued effect of single oral administration on swimming test for ICR mice (n = 12, x̄±SD)

| groups | dosage | swimming test: immobility time(s) |
|---|---|---|
| VIII-9 | 48 mg/kg | 104.3 ± 75.81 |
| | 28.8 mg/kg | 77.4 ± 53.81 |
| | 17.3 mg/kg | 119.4 ± 28.02 |
| | 10.4 mg/kg | 74.3 ± 46.63 |
| VIII-10 | 48 mg/kg | 64.4 ± 43.01 |
| | 28.8 mg/kg | 40.8 ± 40.24** |
| | 17.3 mg/kg | 43.4 ± 35.41** |
| | 10.4 mg/kg | 81.8 ± 39.34 |
| SIPI5286 | 48 mg/kg | 90.1 ± 26.02** |
| | 28.8 mg/kg | 92.1 ± 23.11** |
| | 17.3 mg/kg | 105.4 ± 33.11 |
| | 10.4 mg/kg | 107.9 ± 37.19 |

*$p < 0.05$,
**$p < 0.01$ compared with blank control group

The results of swimming test for ICR mice of single oral administration showed that Compounds VIII-9 and VIII-10 had an equivalent in vivo antidepression activity compared with venlafaxine and SIPI5286, and had a significant difference compared the blank control group. $ED_{50}$ of VIII-9 was 34.3 mg/kg, $ED_{50}$ of VIII-10 was 11.8 mg/kg and $ED_{50}$ of SIPI5286 was 28.9 mg/kg. VIII-10 had the strongest in vivo antidepression activity.

TABLE 6 effect of one week oral administration on swimming test of ICR mice (n = 12, x̄±SD)

| groups | dosage | swimming test: immobility time(s) |
|---|---|---|
| Blank control | N.S | 133.2 ± 35.88 |
| venlafaxine | 50 mg/kg | 83.5 ± 29.0** |
| VIII-9 | 48 mg/kg | 91.5 ± 58.14** |
| | 28.8 mg/kg | 87.2 ± 40.07** |
| | 17.3 mg/kg | 82.1 ± 44.06** |
| | 10.4 mg/kg | 93.4 ± 26.71** |
| VIII-10 | 48 mg/kg | 68.3 ± 34.01** |
| | 28.8 mg/kg | 51.9 ± 51.23** |
| | 17.3 mg/kg | 78.2 ± 25.63** |
| | 10.4 mg/kg | 77.6 ± 24.69** |
| SIPI5286 | 48 mg/kg | 95.5 ± 27.0** |
| | 28.8 mg/kg | 97.2 ± 28.33** |
| | 17.3 mg/kg | 102.9 ± 37.94 |
| | 10.4 mg/kg | 123.8 ± 21.68 |

*$p < 0.05$,
**$p < 0.01$ compared with blank control group

The results of swimming test of one week continuous oral administration for ICR mice also showed that Compound VIII-9 had an equivalent in vivo antidepression activity compared with venlafaxine and SIPI5286, and had a significant difference compared the blank control group. The in vivo antidepression activity of Compound VIII-10 was stronger than that of venlafaxine and SIPI5286.

EXAMPLE 39

Studies on the Acute Toxicity of Compound VIII-9 and VIII-10

Studies on the oral administration acute toxicity in mice of Compound VIII-9 and VIII-10 were performed (Zhang Juntian, Modern Pharmacological Experiments Mothods (last volume), Beijing Medical University and Peking Union Medical University Joint Publishing House, 1998: 1818-1821). The results were shown as below:

| gender | dosage mg/kg | logarithmic dosage | animal number | Death distribution of animals (day) | | | | | | | | number of died animals | mortality (%) | regression rate | $LD_{50}$ (95% confidential limit) mg/kg |
|---|---|---|---|---|---|---|---|---|---|---|---|---|---|---|---|
| | | | | 1 h | 2 h | 4 h | 1 | 4 | 7 | 10 | 14 | | | | |
| male & female VIII-9 | 2844.7 | 3.454 | 6 | 0 | 0 | 0 | 0 | 0 | 0 | 0 | 0 | 0 | 0 | | MLD > 2844.7 mg/kg |
| | 1849.1 | 3.267 | 5 | 0 | 0 | 0 | 0 | 0 | 0 | 0 | 0 | 0 | 0 | | |
| | 1201.9 | 3.0799 | 6 | 0 | 0 | 0 | 0 | 0 | 0 | 0 | 0 | 0 | 0 | | |
| | 781.2 | 2.8928 | 6 | 0 | 0 | 0 | 0 | 0 | 0 | 0 | 0 | 0 | 0 | | |
| | 507.8 | 2.7057 | 6 | 0 | 0 | 0 | 0 | 0 | 0 | 0 | 0 | 0 | 0 | | |
| male & female VIII-10 | 2844.7 | 3.454 | 6 | 0 | 0 | 0 | 6 | 0 | 0 | 0 | 0 | 6 | 100 | 7.2765 | 1048.5 (751.33~1433.7) |
| | 1849.1 | 3.267 | 6 | 0 | 0 | 0 | 5 | 0 | 0 | 0 | 0 | 5 | 83.3 | 6.2940 | |
| | 1201.9 | 3.0799 | 6 | 0 | 0 | 0 | 4 | 0 | 0 | 0 | 0 | 4 | 66.7 | 5.3113 | |
| | 781.2 | 2.8928 | 6 | 0 | 0 | 0 | 2 | 0 | 0 | 0 | 0 | 2 | 33.3 | 4.3286 | |
| | 507.8 | 2.7057 | 6 | 0 | 0 | 0 | 0 | 0 | 0 | 0 | 0 | 0 | 0.00 | 3.3461 | |

Result: After statistically treated by Bliss method, $LD_{50}$ of VIII-10 (95% confidential limit) was 1048.5 (751.33~1433.7) mg/kg, minimum lethal dosage (MLD) of VIII-9 was more than 2844.7 mg/kg. The acute toxicity thereof was lower than that of the preferred compound SIPIyy24 in patent ZL02111934.1 and of the preferred compound SIPI5286 in patent ZL200510030354.1)

EXAMPLE 40

Studies on Pharmacokinetics of Compound VIII-9 and VIII-10

1. Purpose of Test
   To study the pharmacokinetics parameters and the bioavailability of VIII-9, VIII-10 and SIPI5286 when single i.v. and oral administration in SD rat
2. Test Method:
   Eighteen male rats were randomized into 6 groups and were administrated with the three compounds via i.v. and oral route, respectively. The dosage was 10 mg/kg (IV) and 50 mg/kg (PO). The test substance was dissolved in the solution of 5% DMSO/95% HP-β-CD aqueous solution (30%), and were administrated to the animal via i.v. and oral route. Blood plasma was collected at a serial of time points after i.v. and oral administration, and the blood drug concentrations were determined by LC/MS/MS. Then the pharmacokinetics parameters and the bioavailability were calculated based on the blood drug concentrations.

2. Test Results:

| compounds | mode of administration | dosage mg/kg | $C_{max}$ (μg/L) | $T_{max}$ | AUC (0-t) (hr * μg/L) | half life (T½) (hr) | bioavailability |
|---|---|---|---|---|---|---|---|
| VIII-9 | i.v. | 10 | 2640.94 (5 min) | | 4060.59 | 7.83 | |
| | oral | 50 | 352.27 | 1.50 hr | 3345.73 | 5.89 hr | 16.32% |
| VIII-10 | i.v. | 10 | 2998.49 (5 min) | | 2932.05 | 9.06 hr | |
| | oral | 50 | 727.20 | 1.67 hr | 5552.24 | 16.41 hr | 63.78% |
| SIPI5286 | i.v. | 10 | 13876.57 (5 min) | | 12564.22 | 3.41 hr | |
| | oral | 50 | 6856.69 | 0.50 hr | 30255.45 | 5.71 hr | 51.63% |

4. Conclusion

Half life for oral administration of Compound VIII-10 was 16.41 hours, which was longer than that of Compound VIII-9 (5.89 hours) and SIPI5286 (5.71 hours). The bioavailability for oral administration of Compound VIII-10 was 63.78%, which was higher than that of Compound VIII-9 (16.32%) and SIPI5286 (51.63%). Compound VIII-10 has a quite good druggability.

What is claimed is:

1. A 1-butyl-2-hydroxyl aralkyl piperazine derivative, characterized in that, the derivative is the free alkali or its salt of compound of formula (1), or the free alkali or its salt of the optical isomers of compound of formula (1):

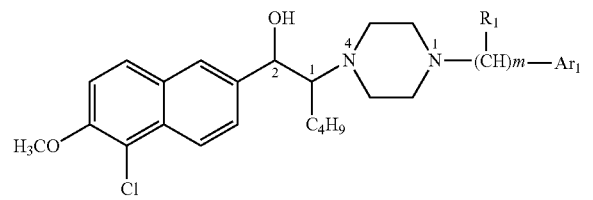

(1)

wherein,
   $Ar_1$ represents benzene, substituted phenyl, a 5-member or 6-member aromatic heterocycle containing N, O or S, or cinnamenyl;
   m is an integer of 0~5;
   $R_1$ represents hydrogen, $C_1$-$C_5$ alkyl, $C_5$ or $C_6$ alicyclic ring, benzene, substituted phenyl, hydroxyl, amino, substituted amino, $C_1$-$C_4$ alkoxy, $C_1$-$C_4$ acyl, halogen, carboxylic acid or carboxylic ester.

2. The 1-butyl-2-hydroxyl aralkyl piperazine derivative according to claim 1, characterized in that, $Ar_1$ represents a substituted phenyl wherein the benzene ring contains one to four substituents and the substituents are halogen, hydroxyl, alkyl, nitro, alkoxy or amino.

3. The 1-butyl-2-hydroxyl aralkyl piperazine derivative according to claim 1, characterized in that, $R_1$ represents a substituted amino wherein the amino contains $C_1$-$C_4$ alkyl, $C_5$ or $C_6$ alicyclic ring, benzene or substituted phenyl as the substituents; wherein the substituted phenyl is a phenyl that contains one to four substituents on the benzene ring, and the substituents are halogen, hydroxyl, alkoxy or amino group.

4. The 1-butyl-2-hydroxyl aralkyl piperazine derivative according to claim 3, characterized in that, the alkyl moiety in $C_1$-$C_5$ alkyl, $C_1$-$C_4$ alkoxy, $C_1$-$C_4$ acyl and $C_5$ or $C_6$ alicyclic ring can be optionally substituted by 1~3 fluorine atoms.

5. The 1-butyl-2-hydroxyl aralkyl piperazine derivative according to claim 1, characterized in that, asymmetric carbon atoms in the structure are achiral or chiral carbon atoms; for chiral carbon atoms, the configuration of chiral carbon atom $C_1$ and $C_2$ are respectively (1S,2R), (1S,2S), (1R,2S) or (1R,2R); wherein, (1SR,2RS) is an erythro isomer and (1SR, 2SR) is a threo isomer.

6. The 1-butyl-2-hydroxyl aralkyl piperazine derivative according to claim 1, characterized in that, the salt is a salt containing the pharmaceutically acceptable anions.

7. The 1-butyl-2-hydroxyl aralkyl piperazine derivative according to claim 6, characterized in that, the salt is hydrochloride, hydrobromide, sulfate, trifluoroacetate or methanesulfonate.

8. The 1-butyl-2-hydroxyl aralkyl piperazine derivative according to claim 1, characterized in that, 0.5~4 molecules of crystal water are contained in the salt.

9. The 1-butyl-2-hydroxyl aralkyl piperazine derivative according to claim 1, which is selected from the group consisting of:
   VIII-1 (1SR,2RS)-$N^1$-p-methoxylphenyl-$N^4$-[1-butyl-2-(5'-chloro-6'-methoxyl-2'-naphthyl)hydroxyethyl]piperazine,
   VIII-2 (1SR,2 SR)-$N^1$-p-methoxylphenyl-$N^4$-[1-butyl-2-(5'-chloro-6'-methoxyl-2'-naphthyl) hydroxyethyl]piperazine,
   VIII-3 (1SR,2RS)-$N^1$-o-methoxylphenyl-$N^4$-[1-butyl-2-(5'-chloro-6'-methoxyl-2'-naphthyl)hydroxyethyl]piperazine,
   VIII-4 (1SR,2SR)-$N^1$-o-methoxylphenyl-$N^4$-[1-butyl-2-(5'-chloro-6'-methoxyl-2'-naphthyl)hydroxyethyl]piperazine,
   VIII-5 (1SR,2RS)-$N^1$-m-chlorophenyl-$N^4$-[1-butyl-2-(5'-chloro-6'-methoxyl-2'-naphthyl)hydroxyethyl]piperazine,
   VIII-6 (1SR,2SR)-$N^1$-m-chlorophenyl-$N^4$-[1-butyl-2-(5'-chloro-6'-methoxyl-2'-naphthyl)hydroxyethyl]piperazine,
   VIII-7 (1SR,2RS)-$N^1$-(2,3-dimethylphenyl)-$N^4$-[1-butyl-2-(5'-chloro-6'-methoxyl-2'-naphthyl)hydroxyethyl] piperazine, VIII-8 (1SR,2SR)-$N^1$-(2,3-dimethylphenyl)-$N^4$-[1-butyl-2-(5'-chloro-6'-methoxyl-2'-naphthyl)hydroxyethyl]piperazine,
VIII-9 (1SR,2RS)-$N^1$-benzyl-$N^4$-[1-butyl-2-(5'-chloro-6'-methoxyl-2'-naphthyl) hydroxyethyl]piperazine,
VIII-10 (1SR,2SR)-$N^1$-benzyl-$N^4$-[1-butyl-2-(5'-chloro-6'-methoxyl-2'-naphthyl) hydroxyethyl]piperazine,
VIII-11 (1SR,2RS)-$N^1$-p-nitrobenzyl-$N^4$-[1-butyl-2-(5'-chloro-6'-methoxyl-2'-naphthyl)hydroxyethyl]piperazine,
VIII-12 (1SR,2SR)-$N^1$-p-nitrobenzyl-$N^4$-[1-butyl-2-(5'-chloro-6'-methoxyl-2'-naphthyl)hydroxyethyl]piperazine,
VIII-13 (1SR,2RS)-$N^1$-p-aminolbenzyl-$N^4$-[1-butyl-2-(5'-chloro-6'-methoxyl-2'-naphthyl)hydroxyethyl]piperazine,
VIII-14 (1SR,2SR)-$N^1$-p-aminolbenzyl-$N^4$-[1-butyl-2-(5'-chloro-6'-methoxyl-2'-naphthyl)hydroxyethyl]piperazine,
VIII-15 (1SR,2RS)-$N^1$-(3',4',5'-trimethoxybenzyl)-$N^4$-[1-butyl-2-(5'-chloro-6'-methoxyl-2'-naphthyl)hydroxyethyl]piperazine,
VIII-16 (1SR,2SR)-$N^1$-(3',4',5'-trimethoxybenzyl)-$N^4$-[1-butyl-2-(5'-chloro-6'-methoxyl-2'-naphthyl)hydroxyethyl]piperazine,
VIII-17 (1SR,2RS)-$N^1$-α-phenemyl-$N^4$-[1-butyl-2-(5'-chloro-6'-methoxyl-2'-naphthyl)hydroxyethyl]piperazine,
VIII-18 (1SR,2SR)-$N^1$-α-phenemyl-$N^4$-[1-butyl-2-(5'-chloro-6'-methoxyl-2'-naphthyl)hydroxyethyl]piperazine,
VIII-19 (1SR,2RS)-$N^1$-benzhydryl-$N^4$-[1-butyl-2-(5'-chloro-6'-methoxyl-2'-Naphthyl)hydroxyethyl]piperazine,
VIII-20 (1SR,2SR)-$N^1$-benzhydryl-$N^4$-[1-butyl-2-(5'-chloro-6'-methoxyl-2'-Naphthyl)hydroxyethyl]piperazine,
VIII-21 (1SR,2RS)-$N^1$-cinnamyl-$N^4$-[1-butyl-2-(5'-chloro-6'-methoxyl-2'-Naphthyl)hydroxyethyl]piperazine,
VIII-22 (1SR,2SR)-$N^1$-cinnamyl-$N^4$-[1-butyl-2-(5'-chloro-6'-methoxyl-2'-naphthyl)hydroxyethyl]piperazine,
IX-23 (1S,2R)-$N^1$-benzyl-$N^4$-[1-butyl-2-(5'-chloro-6'-methoxyl-2'-naphthyl) hydroxyethyl]piperazine,
IX-24 (1S,2S)-$N^1$-benzyl-$N^4$-[1-butyl-2-(5'-chloro-6'-methoxyl-2'-naphthyl) hydroxyethyl]piperazine,
IX-25 (1R,2S)-N-benzyl-$N^4$-[1-butyl-2-(5'-chloro-6'-methoxyl-2'-naphthyl) hydroxyethyl]piperazine, and
IX-26 (1R,2R)-$N^1$-benzyl-$N^4$-[1-butyl-2-(5'-chloro-6'-methoxyl-2'-naphthyl) hydroxyethyl]piperazine.

10. A pharmaceutical composition comprising therapeutically effective amount of 1-butyl-2-hydroxyl aralkyl piperazine derivatives according to claim 1, together with pharmaceutically acceptable carriers.

11. A method for treating depression in a subject, comprising: administering a therapeutically effective amount of the 1-butyl-2-hydroxyl-aralkyl-piperazine derivative of claim 1 to the subject.

\* \* \* \* \*